US006518400B1

(12) United States Patent
Karpen et al.

(10) Patent No.: US 6,518,400 B1
(45) Date of Patent: Feb. 11, 2003

(54) POLYNUCLEOTIDE ENCODING A PROTEIN INVOLVED IN CHROMOSOMAL INHERITANCE AND METHOD OF USE THEREFOR

(75) Inventors: Gary H. Karpen, San Diego, CA (US); Kumar L. Hari, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/534,743

(22) Filed: Mar. 24, 2000

Related U.S. Application Data

(60) Provisional application No. 60/126,954, filed on Mar. 25, 1999.

(51) Int. Cl.⁷ .............................. C07K 14/00

(52) U.S. Cl. ........................ 530/350

(58) Field of Search ......................... 530/350

(56) References Cited

PUBLICATIONS

Cleard et al. (1997. EMBO J. 16(17):5280–5288.*
Harvey, D., et al., Berkeley Drosophila Genome Project, Genomic Sequence, Genbank Accession No. AA439163, obtained from http://www.ncbi.nlm.nih.gov/entrez/>, National Library of Medicine, 2 p., (Nov. 27, 1998).
Afshar, K., et al., "DNA Binding and Meiotic Chromosomal Localization of the Drosophila Nod Kinesin–like Protein", *Cell*, 81 (1), pp. 129–138, (Apr. 7, 1995).
Allshire, R.C., et al., "Mutation derepressing silent centromeric domains in fission yeast disrupt chromosome segregation", *Genes & Development*, 9 (2), pp. 218–233, (Jan. 15, 1995).
Bass, H.W., et al., "Telomeres Cluster De Novo before the Initiation of Synapsis: A Three–dimensional Spatial Analysis of Telomere Positions before and during Meiotic Prophase", *The Journal of Cell Biology*, 137 (1), pp. 5–18, (Apr. 1997).
Bhat, K.M., et al., "The GAGA factor is required in the early Drosophila embryo not only for transcriptional regulation but also for nuclear division", *Development*, 122 (4), pp. 1113–1124, (1996).
Brown, K.E., et al., "Association of Transcriptionally Silent Genes with Ikaros Complexes at Centromeric Heterochromatin", *Cell*, 91 (6), pp. 845–854, (Dec. 12, 1997).
Casso, D., et al., "GFP–tagged balancer chromosome for Drosophila melanogaster", *Mechanisms of Development*, 88 (2), pp. 229–232, (1999).
Chitty, L., "Prenatal Screening for Chromosome Abnormalities", *British Medical Bulletin*, 54 (4), pp. 839–856, (1998).
Chung, C.D., et al., "Specific Inhibition of Stat3 Signal Transduction by PIAS3", *Science*, 278, pp. 1803–1805, (Dec. 5, 1997).

Cook, K.R., et al., "Identification of Trans–Acting Genes Necessary for Centromere Function in Drosophila melangaster Using Centromere–Defective Minichromosomes", *Genetics*, 145 (3), pp. 737–747, (Mar. 1997).
Csink, A.K., et al., "Genetic Modification of Heterochromatic Association and Nuclear Organization in Drosophila", *Nature*, 381 (6582), pp. 529–531, (Jun. 6, 1996).
Dernburg, A.F., et al., "Pertubation of Nuclear Architecture by Long–Distance Chromosome Interactions", *Cell*, 85 (5), pp. 745–759, (May 31, 1996).
Duesberg, P., et al., "How Aneuploidy May Cause Cancer abd Genetic Instability", *Anticancer Research*, 19 (6A), pp. 4887–4906, (1999).
Eissenberg, J.C., et al., "The Heterochromatin–Associated Protein HP–1 is an essential protein in drosophila with dosage–dependent effects on position–effect variegation", *Genetics*, 131, pp. 345–352, (Jun. 1992).
Evans, M.I., et al., "Screening for Aneuploidy", *Current Opinion in Obstetrics and Gynecology*, 11 (2), pp. 115–118, (Apr. 1999).
Fanti, L., et al., "The Heterchromatin Protein 1 Prevents Telomere Fusions in Drosophila", *Molecular Cell*, 2 (5), pp. 527–538, (Nov. 1998).
Goday, C., et al., "Centromere organization in meiotic chromsomes of *Parascaris univalens*", *Chromosoma*, 98 (2), pp. 160–166, (Aug. 1989).
Harper, J.C., et al., "Recent Advances and Future Developments in PGD", *Prenatal Diagnosis*, 19, pp. 1193–1199, (1999).
Harrison, D.A., et al., "Activation of a Drosophila Janus kinase (JAK) causes hematopoietic neoplasia and development defects", *The EMBO Journal*, 14 (12), pp. 2857–2865, (Jun. 15, 1995).
Harrison, D.A., et al., "Drosophila unpaired encodes a secreted protein that activates the JAK signaling pathway", *Genes & Development*, 12 (20), pp. 3252–3263, (Oct. 1998).
Hiraoka, Y., et al., "Focal points for chromosome condensation and decondensation revealed by three–dimensional in vivo time–lapse microscopy", *Nature*, 342, pp. 293–296, (Nov. 16, 1989).
Hou, X.S., et al., "marelle Acts Downstream of the Drosophila HOP/JAK Kinase and Encodes a Protein Similar to the Mammalian STATs", *Cell*, 84 (3), pp. 411–419, (Feb. 1996).
Hyett, J., et al., "First Trimester Screening For Fetal Abnormalities", *Current Opinion in Obstetrics and Gynecology*, 11 (6), pp. 563–569, (Dec. 1999).

(List continued on next page.)

Primary Examiner—Karen Cochrane Carlson
(74) Attorney, Agent, or Firm—Schwegman, Lundberg, Woessner & Kluth, P.A.

(57) ABSTRACT

The invention generally relates to genes that interact with heterochromatin, and more specifically to a suppressor of variegation gene, polypeptide and methods of using the same.

2 Claims, 5 Drawing Sheets

PUBLICATIONS

Jacobs, P.A., et al., "The Origin of Numerical Chromosome Abnormalities", In: *Advances in Genetics*, 33, Chapter 4, Academic Press, Inc., pp. 101–133, (1995).

James, T.C., et al., "Identification of a Nonhistone Chromosomal Protein Associated with Heterochromatin in Drosophila melanogaster and Its Gene", *Molecular and Cellular Biology*, 6 (11), pp. 3862–3872, (Nov. 1986).

Karpen, G.H., et al., "Centric Heteochromatin and the Efficiency of Achiasmate Disjunction in Drosophila Female Meiosis", *Science*, 273, pp. 118–122, (Jul. 5, 1996).

Karpen, G.H., et al., "Reduced DNA Polytenization of a Minichromosome Region Undergoing Position–Effect Variegation in Drosophila", *Cell*, 63, pp. 97–107, (1990).

Kellum, R., et al., "Heterochromatin protein 1 is required for correct chromosome segregation in Drosophila embyros", *Journal of Cell Science*, 108, pp. 1419–1431, (1995).

Liu, B., et al., "Inhibition of Stat1–mediated gene activation by PIAS1", *PNAS*, 95 (18), pp. 10626–10631, (Sep. 1998).

McKee, B.D., et al., "Drosophila Ribosomal RNA Genes Function as an X–Y Pairing Site during male Meiosis", *Cell*, 61, pp. 61–72, (Apr. 1990).

McKenzie, E.A., et al., "The centromere and promoter factor 1, CPF1, of *Saccharomyces cerevisiae* modulates gene activity through a family of factors including SPT21, RPD1 (SIN3), RPD3 and CCR4", *Molecular & General Genetics*, 240, (3), pp. 374–386, (1993).

Mellor, J., et al., "CPF1, a yeast protein which functions in centromeres and promoters", *The EMBO Journal*, 9 (12), pp. 4017–4026, (1990).

Mohr, S.E., et al., "Direct Submission", *Gene*, 229 (1–2), Accession No. AF114486, www.ncbi.nlm.gov:80/entrez/qu . . . ucleotide&list_uids=4761231&dopt=GenBank, pp. 109–116, (1999).

Moilanen, A., et al., "A Testis–specific Androgen Receptor Coregulator That Belongs to a Novel Family of Nuclear Proteins", *The Journal of Biological Chemistry*, 274 (6), pp. 3700–3704, (Feb. 5, 1999).

Munne, S., et al., "Chromosome abnormalities in human embryos", *Human Reproduction update*, 4 (6), pp. 842–855, (1998).

Murphy, T.D., et al., "Interactions between the nod+ Kinesin–like Gene and Extracentromeric Sequences Are Required for Transmission of a Drosophila Minichromosome", *Cell*, 81 (1), pp. 139–148, (Apr. 7, 1995).

Platero, J.S., et al., "Changes in Chromosomal Localization of Heterochromatin–binding Proteins during the Cell Cycle in Drosophila", *The Journal of Cell Biology*, 140 (6), pp. 1297–1306, (Mar. 23, 1998).

Pluta, A.F., et al., "Specific Interaction between Human Kinetochore Protein CENP–C and a Nucleolar Transcriptional Regulator", *The Journal of Biological Chemistry*, 271 (31), pp. 18767–18774, (1996).

Sen, S., "Aneuploidy and Cancer", *Current Opinion in Oncology*, 12 (1), pp. 82–88, (Jan. 2000).

Torok, T., et al., "The Product of proliferation disrupter is concentrated at centromeres and required for mitotic chromosome condensation and cell proliferation in Drosophila", *Gene & Development*, 11, pp. 213–225, (Jan. 15, 1997).

Tsukiyama, T., et al., "ATP–dependent nucleosome disruption at a heat–shock promoter mediated by binding of GAGA transcription factor", *Nature*, 367 (6463), pp. 525–532, (Feb. 10, 1994).

Valdez, B.C., et al., "Cloning and Characterization of Gu/RH–II Binding Protein", *Biochemical and Biophysical Research Communications*, 234 (2), pp. 335–340, (1997).

Wakimoto, B.T., "Beyond the Nucleosome: Epigenetic Aspects of Position—Effect Variegation in Drosophila", *Cell*, 93 (3), pp. 321–324, (May 1, 1998).

Wakimoto, B.T., et al., "The Effects of Chromosome Rearrangements on the Expression of Heterochromatic Genes in Chromosome 2L of Drosophila melanogaster", *Genetics*, 125 (1), pp. 141–154, (1990).

Williams, S.M., et al., "Molecular genetic analysis of Drosophila rDNA arrays", *Trends in Genetics*, 8 (10), pp. 335–340, (Oct. 1992).

Wines, D.R., et al., "Somatic Instability of a Drosophila Chromosome", *Genetics*, 131 (3), pp. 683–691, (Jul. 1992).

Wu, L., et al., "Miz1, a novel zinc finger transcription factor that interacts with Msx2 and enhances its affinity for DNA", *Mechanism of Development*, 65 (1,2), pp. 3–17, (Jul. 1997).

Yan, R., et al., "Identification of a Stat Gene Tha Functions in Drosophila Development", *Cell*, 84 (3), pp. 421–430, (Feb. 1996).

Aagaard, et al., "Functional mammalian homologues of the Drosophila PEV–modifier Su(var) 3–9 encode centromere–associated proteins which complex with the heterochromatin component M31," *The EMBO Journal* 18(7):1923–1938 (1999).

Mohr and Boswell, "Zimp encodes a homologue of mouse Miz1 and PIAS3 and is an essential gene in *Drosophila melanogaster*," *Gene* 229:109–118 (1999).

Spradling, et al., "The Berkeley Drosophila Genome Project Gene Disruption Project: Single P–Element Insertions Mutating 25% of Vital Drosophila Genes," *Genetics* 153:135–177 (1999).

Lori L. Wallrath, "Unfolding the mysteries of heterochromatin," *Current Opinion in Genetics & Development* 8:147–153 (1998).

Wustmann, et al., "The genetics of position—effect of variegation modifying loci in *Drosophila melanogaster*," *Mol Gen Genet* 217:520–527 (1989).

\* cited by examiner

Su(var)2-10¹ (T to A change at base 979)
```
ATGGTGCAGA TGCTTCGAGT GGTCGAGCTG CAAAAAATCC TGTCGTTTCT  50
GAACATCTCA TTCGCTGGAC GAAAAACTGA CCTGCAGAGC CGCATCCTCT 100
CGTTCTTGCG CACCAACTTG GAACTGCTTG CCCCGAAGGT CCAGGAAGTC 150
TACGCCCAGT CCGTGCAGGA ACAAAACGCC ACGCTGCAGT ACATCGACCC 200
AACCAGGATG TACTCGCACA TCCAGCTGCC GCCCACCGTG CAGCCCAATC 250
CCGTGGGCCT CGTGGGCAGC GGCCAAGGTG TGCAAGTGCC CGGCGGCCAG 300
ATGAATGTGG TCGGCGGCGC ACCCTTCCTC CACACACACA GCATCAACAG 350
CCAGCTGCCT ATTCACCCCG ATGTGCGGCT GAAAAAGCTA GCCTTCTACG 400
ATGTACTCGG AACGCTAATT AAGCCTTCAA CTCTGGTGCC ACGCAACACT 450
CAGCGCGTCC AAGAGGTGCC TTTCTACTTC ACGCTCACGC CGCAGCAGGC 500
CACCGAGATT GCCTCCAATC GCGACATTCG CAACAGCTCC AAGGTGGAGC 550
ACGCCATTCA GGTTCAACTG CGCTTTTGCC TGGTGGAGAC TTCGTGCGAC 600
CAGGAGGACT GCTTCCCGCC GAACGTAAAC GTCAAAGTGA CAACAAACT 650
CTGTCAGCTG CCTAATGTCA TTCCTACAAA CCGACCAAAT GTGGAGCCCA 700
AGCGTCCGCC GCGACCCGTT AATGTCACGT CCAATGTAAA GCTGTCGCCT 750
ACCGTCACCA ACACCATAAC GGTTCAGTGG TGTCCGGACT ACACTCGTAG 800
CTACTGTCTG GCCGTATACC TGGTAAAGAA GCTCACCTCA ACACAGCTTT 850
TGCAGCGAAT GAAGACGAAG GGCGTAAAAC CAGCGGACTA CACGCGAGGC 900
TTAATCAAAG AGAAGCTGAC TGAGGATGCT GACTGCGAAA TAGCCACCAC 950
TATGCTGAAG GTTTCCCTTA ACTGCCGAT GGGCAAGATG AAAATGTTGC 1000
TGCCTTGTCG AGCATCAACC TGCTCGCATC TGCAATGCTT CGATGCCAGT 1050
CTCTACCTGC AAATGAATGA GCGTAAGCCC ACGTGGAACT GCCCTGTATG 1100
CGACAAGCCG GCCATTTATG ACAACCTGGT CATAGATGGC TACTTCCAGG 1150
AGGTGTTGGG CTCGTCGCTT CTAAAGAGTG ATGATACTGA GATTCAACTT 1200
CATCAGGATG GATCTTGGAG CACACCAGGA TTACGGAGCG AGACGCAGAT 1250
CCTTGATACG CCTTCAAAGC CCGCCCAAAA GGTTGAGGTT ATATCGGATG 1300
ACATAGAACT TATCTCGGAT GACGCCAAGC CAGTAAAGAG GGATTTGTCC 1350
CCAGCACAGG ACGAACAGCC CACATCAACG TCAAACAGTG AAACTGTTGA 1400
CCTAACGTTA AGCGATTCAG ACGACGACAT GCCGCTGGCT AAGCGTTGTC 1450
CGCCCGCCAA GCAAGCCGTC GCCAGTTCCA CGTCGAACGG CAGCGGTGGC 1500
GGCCAACGTG CCTATACCCC GGCACAGCAG CCCCAGCAAT CCGAGGATAA 1550
TGACGAAAAC TGTATGGCTA AGGCCAAAGA GGATTCCGTA ATTGATTTTT 1600
TAGATTCGCC A   1611
```

Su(var)2-10² (G to A change at base 780)
```
ATGGTGCAGA TGCTTCGAGT GGTCGAGCTG CAAAAAATCC TGTCGTTTCT  50
GAACATCTCA TTCGCTGGAC GAAAAACTGA CCTGCAGAGC CGCATCCTCT 100
CGTTCTTGCG CACCAACTTG GAACTGCTTG CCCCGAAGGT CCAGGAAGTC 150
TACGCCCAGT CCGTGCAGGA ACAAAACGCC ACGCTGCAGT ACATCGACCC 200
AACCAGGATG TACTCGCACA TCCAGCTGCC GCCCACCGTG CAGCCCAATC 250
CCGTGGGCCT CGTGGGCAGC GGCCAAGGTG TGCAAGTGCC CGGCGGCCAG 300
ATGAATGTGG TCGGCGGCGC ACCCTTCCTC CACACACACA GCATCAACAG 350
CCAGCTGCCT ATTCACCCCG ATGTGCGGCT GAAAAAGCTA GCCTTCTACG 400
ATGTACTCGG AACGCTAATT AAGCCTTCAA CTCTGGTGCC ACGCAACACT 450
CAGCGCGTCC AAGAGGTGCC TTTCTACTTC ACGCTCACGC CGCAGCAGGC 500
CACCGAGATT GCCTCCAATC GCGACATTCG CAACAGCTCC AAGGTGGAGC 550
ACGCCATTCA GGTTCAACTG CGCTTTTGCC TGGTGGAGAC TTCGTGCGAC 600
CAGGAGGACT GCTTCCCGCC GAACGTAAAC GTCAAAGTGA CAACAAACT 650
CTGTCAGCTG CCTAATGTCA TTCCTACAAA CCGACCAAAT GTGGAGCCA 700
AGCGTCCGCC GCGACCCGTT AATGTCACGT CCAATGTAAA GCTGTCGCCT 750
ACCGTCACCA ACACCATAAC GGTTCAGTGA TGTCCGGACT ACACTCGTAG 800
CTACTGTCTG GCCGTATACC TGGTAAAGAA GCTCACCTCA ACACAGCTTT 850
```

FIGURE 4A

```
TGCAGCGAAT GAAGACGAAG GGCGTAAAAC CAGCGGACTA CACGCGAGGC    900
TTAATCAAAG AGAAGCTGAC TGAGGATGCT GACTGCGAAA TAGCCACCAC    950
TATGCTGAAG GTTTCCCTTA ACTGCCCGTT GGGCAAGATG AAAATGTTGC   1000
TGCCTTGTCG AGCATCAACC TGCTCGCATC TGCAATGCTT CGATGCCAGT   1050
CTCTACCTGC AAATGAATGA GCGTAAGCCC ACGTGGAACT GCCCTGTATG   1100
CGACAAGCCG GCCATTTATG ACAACCTGGT CATAGATGGC TACTTCCAGG   1150
AGGTGTTGGG CTCGTCGCTT CTAAAGAGTG ATGATACTGA GATTCAACTT   1200
CATCAGGATG GATCTTGGAG CACACCAGGA TTACGGAGCG AGACGCAGAT   1250
CCTTGATACG CCTTCAAAGC CCGCCCAAAA GGTTGAGGTT ATATCGGATG   1300
ACATAGAACT TATCTCGGAT GACGCCAAGC CAGTAAAGAG GGATTTGTCC   1350
CCAGCACAGG ACGAACAGCC CACATCAACG TCAAACAGTG AAACTGTTGA   1400
CCTAACGTTA AGCGATTCAG ACGACGACAT GCCGCTGGCT AAGCGTTGTC   1450
CGCCCGCCAA GCAAGCCGTC GCCAGTTCCA CGTCGAACGG CAGCGGTGGC   1500
GGCCAACGTG CCTATACCCC GGCACAGCAG CCCCAGCAAT CCGAGGATAA   1550
TGACGAAAAC TGTATGGCTA AGGCCAAAGA GGATTCCGTA ATTGATTTTT   1600
TAGATTCGCC A    1611
```

SU(VAR)2-10[1] (Leucine to Methionine change at amino acid 327)
```
MVQMLRVVEL QKILSFLNIS FAGRKTDLQS RILSFLRTNL ELLAPKVQEV    50
YAQSVQEQNA TLQYIDPTRM YSHIQLPPTV QPNPVGLVGS GQGVQVPGGQ   100
MNVVGGAPFL HTHSINSQLP IHPDVRLKKL AFYDVLGTLI KPSTLVPRNT   150
QRVQEVPFYF TLTPQQATEI ASNRDIRNSS KVEHAIQVQL RFCLVETSCD   200
QEDCFPPNVN VKVNNKLCQL PNVIPTNRPN VEPKRPPRPV NVTSNVKLSP   250
TVTNTITVQW CPDYTRSYCL AVYLVKKLTS TQLLQRMKTK GVKPADYTRG   300
LIKEKLTEDA DCEIATTMLK VSLNCPMGKM KMLLPCRAST CSHLQCFDAS   350
LYLQMNERKP TWNCPVCDKP AIYDNLVIDG YFQEVLGSSL LKSDDTEIQL   400
HQDGSWSTPG LRSETQILDT PSKPAQKVEV ISDDIELISD DAKPVKRDLS   450
PAQDEQPTST SNSETVDLTL SDSDDDMPLA KRCPPAKQAV ASSTSNGSGG   500
GQRAYTPAQQ PQQSGDNDEN CMAKAKEDSV IDFLDSP    537

MVQMLRVVEL QKILSFLNIS FAGRKTDLQS RILSFLRTNL ELLAPKVQEV    50
YAQSVQEQNA TLQYIDPTRM YSHIQLPPTV QPNPVGLVGS GQGVQVPGGQ   100
MNVVGGAPFL HTHSINSQLP IHPDVRLKKL AFYDVLGTLI KPSTLVPRNT   150
QRVQEVPFYF TLTPQQATEI ASNRDIRNSS KVEHAIQVQL RFCLVETSCD   200
QEDCFPPNVN VKVNNKLCQL PNVIPTNRPN VEPKRPPRPV NVTSNVKLSP   250
TVTNTITVQW CPDYTRSYCL AVYLVKKLTS TQLLQRMKTK GVKPADYTRG   300
LIKEKLTEDA DCEIATTMLK VSLNCPMGKM KMLLPCRAST CSHLQCFDAS   350
LYLQMNERKP TWNCPVCDKP AIYDNLVIDG YFQEVLGSSL LKSDDTEIQL   400
HQDGSWSTPG LRSETQILDT PSKPAQKVEV ISDDIELISD DAKPVKRDLS   450
PAQDEQPTST SNSETVDLTL SDSDDDMPLA KRCPPAKQAV ASSTSNGSGG   500
GQRAYTPAQQ PQQSGSPEQQ ASRQSPEKQT VSEQQLQQQQ HEQPATAAVH   550
ASLLESLAAA VADQKHFQLL DLAAVAAAAA ATASSGQSQN AGP    593
```

SU(VAR)2-10[2] (Tryptophan to STOP change at amino acid 260)
```
MVQMLRVVEL QKILSFLNIS FAGRKTDLQS RILSFLRTNL ELLAPKVQEV    50
YAQSVQEQNA TLQYIDPTRM YSHIQLPPTV QPNPVGLVGS GQGVQVPGGQ   100
MNVVGGAPFL HTHSINSQLP IHPDVRLKKL AFYDVLGTLI KPSTLVPRNT   150
QRVQEVPFYF TLTPQQATEI ASNRDIRNSS KVEHAIQVQL RFCLVETSCD   200
QEDCFPPNVN VKVNNKLCQL PNVIPTNRPN VEPKRPPRPV NVTSNVKLSP   250
TVTNTITVQ    259

MVQMLRVVEL QKILSFLNIS FAGRKTDLQS RILSFLRTNL ELLAPKVQEV    50
YAQSVQEQNA TLQYIDPTRM YSHIQLPPTV QPNPVGLVGS GQGVQVPGGQ   100
MNVVGGAPFL HTHSINSQLP IHPDVRLKKL AFYDVLGTLI KPSTLVPRNT   150
QRVQEVPFYF TLTPQQATEI ASNRDIRNSS KVEHAIQVQL RFCLVETSCD   200
QEDCFPPNVN VKVNNKLCQL PNVIPTNRPN VEPKRPPRPV NVTSNVKLSP   250
TVTNTITVQ    259
```

FIGURE 4B

POLYNUCLEOTIDE ENCODING A PROTEIN INVOLVED IN CHROMOSOMAL INHERITANCE AND METHOD OF USE THEREFOR

CROSS REFERENCE TO RELATED APPLICATIONS

This application claims priority under 35 U.S.C. §119(e)(1) to U.S. Provisional Application 60/126,954, filed Mar. 25, 1999, the disclosure of which is herein incorporated by reference in its entirety.

STATEMENT REGARDING FEDERALLY SPONSORED RESEARCH

This invention was funded in part by National Institutes of Health Grant Nos. GM 54549 and CA64041. The government may have certain rights in the invention

FIELD OF THE INVENTION

The invention relates generally to chromosome inheritance and cell proliferative disorders and more specifically to a polypeptide and a polynucleotide that encodes a polypeptide that affects organization of chromosomes within the nucleus and methods of use therefor.

BACKGROUND

Eukaryotic organisms package DNA via nucleosomes into highly organized and dynamic chromosomes. During the mitotic cell division cycle the chromosomes must first be completely replicated after which the newly formed sister chromatids condense and are segregated equally to the daughter nuclei. After cytokinesis the whole chromosome cycle is ready to be reinitiated. Pre-meiotic replication results in two sets of sister chromatids. During the first meiotic division it is the paired homologs (two sets of sister chromatids) which segregate from each other, then the sister chromatids are separated into four daughter nuclei of the gametes (spores in yeast). These events are highly conserved and occur in all eukaryotes from unicellular yeast to humans.

There are three cis acting elements which are essential to the chromosome cycle in any eukaryote: replication origins, telomeres, and centromeres. Replication is initiated during S-phase from the replication origins. These regions of the chromosome ensure that the chromosomes are completely replicated before the cell embarks on mitosis. Telomeres are specialized structures which allow complete replication of the ends of chromosomes and protect them from erosion and fusion with other DNA fragments. A centromere is a cis-acting DNA element where protein factors required for mitotic and meiotic chromosome transmission (collectively termed the kinetochore) are assembled. Centromeres act as the nucleation point for kinetochore formation and attachment of the sister chromatids to microtubules emanating from each pole of the spindle. The centromeres, in conjunction with normal spindle formation, are responsible for the delivery of a complete set of chromosomes to the daughter nuclei. The kinetochore mediates attachment of the chromosomes to spindle microtubules during mitosis and ensures that each daughter cell receives a complete set of chromosomes. Centromere malfunction results in the loss of or gain of chromosomes, i.e., aneuploidy, which is associated with 45% of spontaneous abortions in humans (Jacobs and Hassold (1995), Ads. Genet. 33, 101–132). In addition, aneuploidy is commonly observed in human cancer (Duesberg et al. *Anticancer Res* 1999 November-December; 19(6A):4887–906; Sen S., *Curr Opin Oncol* 2000 January; 12(1):82–8).

Heterochromatin is an enigmatic component of higher eukaryotic genomes. The paucity of genes and abundance of repetitive sequence in heterochromatin contribute to it being described as functionally inert. However, heterochromatin houses essential single copy loci (Wakimoto, B. T., and Hearn, M. G. (1990), Genetics 125, 141–54) and the rDNA loci, the most highly transcribed genes in the genome (reviewed in Williams, S. M., and Robbins, L. G. (1992), Trends Genet 8, 335–40). In addition, the centromere, the site of kinetochore formation, spindle attachment and checkpoint control during mitosis and meiosis is usually buried deep within heterochromatin. Elegant studies from a variety of organisms (Bass et al. (1997), J Cell Biol 137, 5–18; Goday, C., and Pimpinelli, S. (1989), Chromosoma 98, 160–6) indicate that heterochromatin plays other important roles in chromosome inheritance. For example, heterochromatic homology is required for faithful homolog pairing and chromosome segregation during male and female meiosis in Drosophila (Dernburg et al., (1996), Cell 85, 745–59; Karpen et al. (1996), Science 273, 118–22; McKee, B. D., and Karpen, G. H. (1990), Cell 61, 61–72). While these analyses have highlighted essential roles for heterochromatin in inheritance functions, more detailed dissections will entail characterizing the specific gene products that control heterochromatin metabolism and chromosome inheritance.

SUMMARY OF THE INVENTION

The conserved heterochromatic location of higher eukaryotic centromeres suggests that intrinsic properties of heterochromatin are important for chromosome inheritance. Based on this hypothesis, mutations in Drosophila melanogaster that alter heterochromatin-induced gene silencing were tested for effects on chromosome inheritance. The invention provides cloning and characterization of the Su(var)2–10 locus, initially identified as a Suppressor of Position Effect Varegation. Su(var)2–10 is required for viability, and mutations cause both minichromosome and endogenous chromosome inheritance defects. These defects include the hypocondensation of mitotic chromosomes and disruptions in the nuclear organization of interphase chromosomes. The Su(var)2–10 locus encodes a member of the PIAS/ARIP3/Miz1 protein family, a highly conserved group with diverse functions. Accordingly, the invention encompasses these related members of the family and methods of using these related members. Despite multiple chromosomal phenotypes SU(VAR)2–10 protein is not found in mitotic chromosomes. Instead, the protein colocalizes with lamin at the nuclear membrane and surrounds or sheaths interphase polytene chromosomes. Su(var)2–10 provides a mechanistic link between nuclear organization, gene expression and chromosome inheritance.

Su(var)2–10 mutants exhibit multiple phenotypes, including dominant alterations in minichromosome inheritance and heterochromatin-induced gene silencing, and recessive lethality, endogenous chromosome inheritance defects and melanotic tumors.

In one embodiment, the invention provides an isolated polypeptide characterized as modulating heterochromatin-induced gene silencing; and which is required for chromosome inheritance.

In another embodiment, the invention provides an isolated polynucleotide encoding a polypeptide characterized as modulating heterochromatin-induced gene silencing; and which is required for chromosome inheritance. In one embodiment, the polypeptide has a sequence as set forth in SEQ ID NO:2 or 4.

In yet another embodiment, the invention provides a transgenic organism having a transgene disrupting expression of a polynucleotide sequence encoding encoding a Su(var)2–10 polypeptide, or conservative variations thereof, wherein the polynucleotide is chromosomally integrated into the germ cells of the organism.

In yet another embodiment, the invention provides a nucleic acid construct comprising a disrupted polynucleotide sequence encoding SEQ ID NO:2 or 4, wherein the polynucleotide sequence is disrupted by integration of nucleic acid sequence which inhibits expression of a functional gene product.

In another embodiment, the invention provides a method of producing a transgenic organism, comprising: introducing in the genome of the organism a nucleic acid construct comprising a disrupted polynucleotide sequence encoding SEQ ID NO:2 or 4, wherein the polynucleotide sequence is disrupted by integration of nucleic acid sequence which inhibits expression of a functional gene product operably linked to a promoter which functions in the organism to cause the production of an RNA sequence; and obtaining a transgenic organism having a disrupted polynucleotide sequence encoding wild type Su(var)2–10.

In yet another embodiment, the invention provides a transgenic organism encoding the polypeptide sequence of SEQ ID Nos.2 or 4, operably linked to a conditional promoter, chromosomally integrated into the germ cells of the insect.

In another embodiment, the invention provides an insecticide composition, comprising a nucleic acid construct comprising a disrupted polynucleotide sequence encoding SEQ ID NO:2 or 4, wherein the polynucleotide sequence is disrupted by integration of nucleic acid sequence which inhibits expression of a functional gene product and an agriculturally acceptable carrier.

In another embodiment, the invention provides an antibody which interacts with a Su(var)2–10 polypeptide or binds to an antigenic fragment of a Su(var)2–10 polypeptide.

In yet another embodiment, the invention provides a method of identifying an agent which modulates a Su(var)2–10 polypeptide activity, by incubating the agent and the polypeptide or a recombinant cell expressing the polypeptide, under conditions sufficient to allow the components to interact; and determining the effect of the agent on the activity of the polypeptide or the polypeptide's expression compared to a control.

In yet another embodiment, the invention provides a method of detecting or diagnosing a cell proliferative disorder in a sample, comprising contacting the sample with an agent which detects a mutant Su(var)2–10, wherein the presence of the mutant Su(var)2–10 is indicative of a cell proliferative disorder.

BRIEF DESCRIPTION OF THE FIGURES

FIGS. 2–2E shows the molecular analysis of the 15 kb genomic rescue construct. A) The 15 kb genomic fragment used to create the Su(var)2–10+ transgene is shown, as is the insertion site of the Su(var)2–10$^{03697}$ P element. B) The direction and extent of the imprecise P element excision Su(var)2–10$^{Pex74A}$. C) The 5 kb of genomic DNA isolated from plasmid rescue experiments and used in cDNA library screening and Southern blot analyses. D) The location and organization of transcription units present in the genomic rescue fragment. The Su(var)2–10 transcript is highlighted by thick blue bars. Light blue bars indicate 5' and 3' UTR, while dark blue indicates the ORFs. The location of translational start (AUG) and stop codons (stop signs) are indicated above the transcript, and the nucleotide changes yielding mutations for the Su(var)2–101 and Su(var)2–102 allele are indicated below the transcript. E) Rescuing the variegation phenotype of Su(var)2–10. Flies of the indicated genotype are shown. Note the similarly reduced w+ expression in the top two flies, indicating rescue of the dominant PEV suppression phenotype.

FIGS. 4A–B shows the polynucleotide and polypeptide sequences of Su(var)2–10$^1$ and Su(var)2–10$^2$.

DETAILED DESCRIPTION OF THE INVENTION

Figure 1:
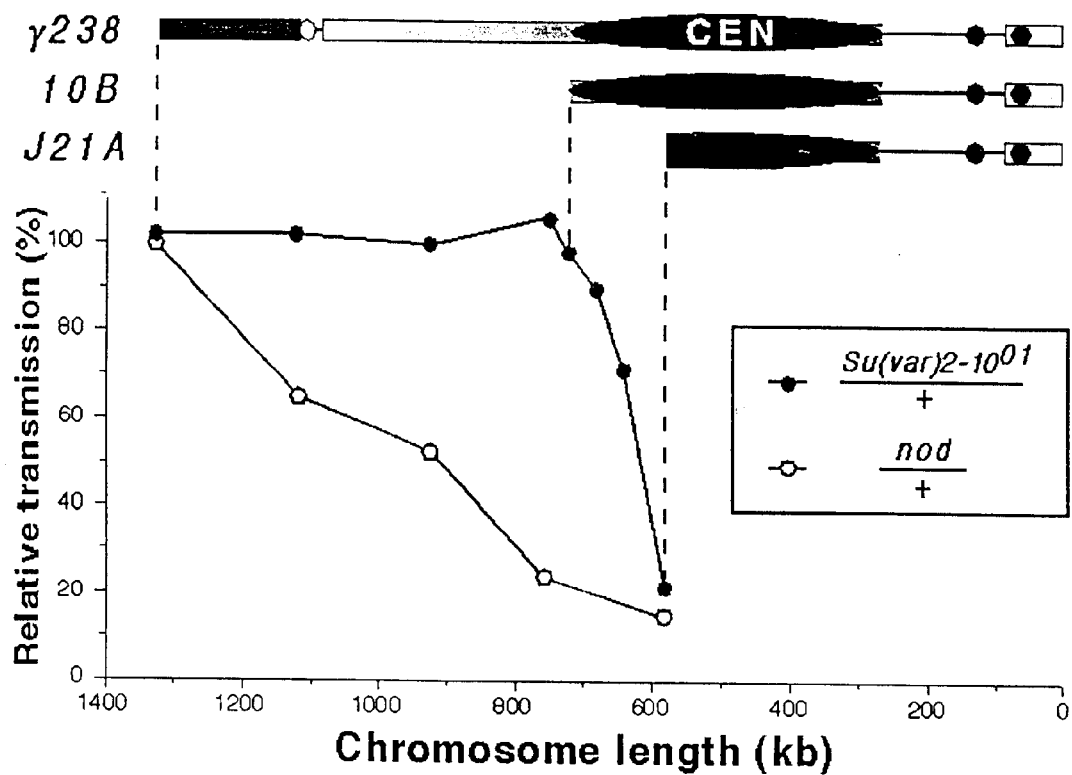
FIG. 1 shows that Su(var)2–10 interacts genetically with the 420 kb minichromosome centromere and not with extracentromeric DNA. The transmission rates of a subset of Dpi 187 derivatives in a Su(var)2–10+ background are compared to their transmission in a standard wild type background. Both EMS alleles of Su(var)2–10 exhibit centromere-specific genetic interaction patterns. Transmission rates are plotted relative to the transmission rate for each minichromosome in standard background. Immediate decreases are seen in the relative transmission of derivatives in a nod+ background, and that no decreases occur for derivatives in a Su(var)2–10+ background until portions of the centromere are deleted.

Heterochromatin can silence the expression of genes that are normally found in euchromatin, resulting in a phenomenon known as Position Effect Variegation (PEV). PEV manifests as the mosaic or variegated expression of an affected locus due to the abnormal juxtaposition of euchromatic genes with centric heterochromatin and telomeres (Wallrath, L. L. (1998), Curr Opin Genet Dev 8, 147–53). Changes in the chromatin structure surrounding a variegating gene may cause "spreading" of the heterochromatic state into neighboring regions of euchromatin (reviewed in Wakimoto, B. T. (1998), Cell 93, 321–4). However, PEV also occurs when heterochromatic associations produce large-scale alterations in the nuclear organization of chromosomes. For example, a large block of heterochromatin inserted into the Drosophila brown (bw) gene induces the mislocalization of a normal, paired copy of the locus to a region of the nucleus containing centric heterochromatin (Csink, A. K., and Henikoff, S. (1996), Nature 381, 529–31;

Dernburg et al., (1996), Cell.85, 745–59). Similarly, in interphase nuclei of mammalian B lymphocytes, Ikaros proteins that are essential for lymphocyte development localize to centric heterochromatin, and silencing of lymphoid-associated genes correlates with their association with Ikaros (Brown et al., (1997), Cell 91, 845–54). These data demonstrate that the nuclear organization of genes and chromosomes also contributes to PEV.

The methods and composition of the invention are based on a method, devised by the inventor, to systematically screen Drosophila PEV modifiers for roles in chromosome inheritance. J21A, one of a large collection of Dp(1;f)01187 (Dp1187) minichromosome derivatives, is a centromere-defective, non essential minichromosome that is transmitted to progeny with half the frequency of fully-functional min-ichromosomes. This substrate is "sensitized" to the altered dosage of inheritance proteins (Cook et al. (1997), Genetics 145, 737–47; Murphy, T. D., and Karpen, G. H. (1995), Cell 81, 139–48) and its loss yields no deleterious effects on organismal viability. Thus, J21A was used to screen for dominant effects of mutations on transmission, bypassing the aneuploidy-induced lethality that can result when screening for mutations that impact endogenous chromosome inheritance. The invention demonstrates that nearly half of Su(var) and E(var) mutations dominantly alter the transmission of J21A, suggesting that a large proportion of PEV modifier loci play a role in inheritance. The cloning and characterization of loci identified in this screen, Su(var)2–10 is described herein. The invention provides a polynucleotide and polypeptide sequence and methods based on the discovery that Su(var)2–10 is required for chromosome inheritance functions as well as proper chromosome structure and function. Furthermore, Su(var)2–10 plays a role in multiple cellular tasks through effects on the organization of chromosomes within the nucleus.

The present invention provides polypeptides and polynucleotides associated with chromosomal inheritance, wherein an isolated polypeptide of the invention is characterized as modulating heterochromatin gene silencing and is required for proper chromosome inheritance.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions).

Polynucleotide or nucleic acid sequence refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of the of the polynucleotide sequence. Both constitutive and inducible promoters, are included in the invention (see e.g., Bitter et al., Methods in Enzymology 153:516–544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding a Su(var)2–10 polypeptide of fragment thereof The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide of the invention such that the localization or signal peptide is located at the amino terminal end of a resulting polynucleotide/polypeptide. The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp.516–544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673–684, 1987; and The Molecular Biology of the Yeast Saccharomyces, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system which could be used to express a Su(var)2–10 polypeptide of the invention is an insect system. In one such system, *Autographa californica* nuclear polyhedrosis virus (AcNPV) is used as a vector to express foreign or mutated polynucleotide sequences. The virus grows in *Spodoptera frugiperda* cells. The sequence encoding a protein of the invention may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., J. Viol. 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a Su(var)2–10 polypeptide or fragment thereof.

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a Su(var)2–10 polypeptide and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., Drosophila sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, a polynucleotide encoding a Su(var)2–10 may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a Su(var)2–10 polypeptide or fragment thereof in infected hosts (e.g., see Logan & Shenk, Proc. Natl. Acad. Sci. USA, 81:3655–3659, 1984). Alternatively, the vaccinia virus 7.5K promoter may be used. (e.g., see, Mackett, et al., Proc. Natl. Acad. Sci. USA, 79:7415–7419, 1982; Mackent, et al., J. Virol. 49:857–864, 1984; Panicali, et al., Proc. Natl. Acad. Sci. USA 79:4927–4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a Su(var)2–10 gene in host cells (Cone & Mulligan, Proc. Natl. Acad. Sci. USA, 81:6349–6353, 1984). High level expression may also be achieved using inducible promoters, including, but not limited to, the metallothionine IIA promoter and heat shock promoters.

For long-term, high-yield production of recombinant proteins, stable expression is preferred. Rather than using expression vectors which contain viral origins of replication, host cells can be transformed with the cDNA encoding a Su(var)2–10 polypeptide controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1–2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt- cells respectively. Also, anti-metabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 198 1); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol. 150:1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product which is complementary to a nucleic acid strand is initiated in the presence of nucleoside triphosphates and a polymerase in an appropriate buffer at a suitable temperature. For instance, if a nucleic acid sequence is inferred from a protein sequence, a primer generated to synthesize nucleic acid sequence encoding the protein sequence. is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences. For example, primers can be synthesized based upon the amino acid sequence as set forth in SEQ ID NO:2 or 4 and can be designed based upon the degeneracy of the genetic code.

A polypeptide or protein refers to a polymer in which the monomers are amino acid residues which are joined together through amide bonds. When the amino acids are alpha-amino acids, either the L-optical isomer or the D-optical isomer can be used, the L-isomers being typical. A Su(var) 2–10 polypeptide is intended to encompass any amino acid sequence and include modified sequences such as glycoproteins, which provides a polypeptide having Su(var) 2–10 activity. Accordingly, the polypeptides of the invention are intended to cover naturally occurring proteins, as well as those which are recombinantly or synthetically synthesized. In addition, a Su(var)2–10 polypeptide can occur in at least two different conformations wherein both conformations have the same or substantially the same amino acid sequence but have different three dimensional structures so long as the have a biological activity related to Su(var)2–10. Polypeptide or protein fragments of Su(var)2–10 are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general, two amino acid sequences are substantially the same or substantially homologous if they are at least 70% identical.

A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

Su(var)2–10 Polynucleotides, Polypeptides and Method of Expression

In one embodiment, the invention provides an isolated polynucleotide sequence encoding a Su(var)2–10 polypeptide. A Su(var)2–10 polypeptide can be characterized by one or more of the following: (1) its ability to modulate heterochromatin-induced gene expression; (2) necessary for chromosome inheritance; (3) colocalizes with lamin in the nuclear periphery during interphase; (4) surrounds chromosomes in polytene nuclei; and (5) about 60 kDa by relative mobility shift as measured by SDS-PAGE. An exemplary Su(var)2–10 polypeptide of the invention has an amino acid sequence as set forth in SEQ ID NO:2 or 4. Polynucleotide sequences of the invention include DNA, cDNA and RNA sequences which encode Su(var)2–10 as well as complementary sequences thereof. It is understood that all polynucleotides encoding all or a portion of Su(var)2–10 are also included herein, so long as they encode a polypeptide with Su(var)2–10 activity (e.g., modulation of heterochromatin-induced gene expression, plays a role in chromosome inheritance). Such polynucleotides include naturally occurring, synthetic, and intentionally manipulated polynucleotides. For example, Su(var)2–10 polynucleotide may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of Su(var)2–10 polypeptide encoded by the nucleotide sequence is functionally unchanged. Also included are nucleotide sequences which encode Su(var)2–10 polypeptide, such as SEQ ID NO:1 and 3. In addition, the invention also includes a polynucleotide encoding a polypeptide having the biological activity of an amino acid sequence of SEQ ID NO:2 and 4 and having at least one epitope for an antibody immunoreactive with Su(var)2–10 polypeptide. However, it is recognized that portions of any of the sequences (e.g., SEQ ID NO's:1–5) may be excluded to identify fragments of the polynucleotide sequence or polypeptide sequence. For example, polypeptide fragments of SEQ ID NO:2 and 4, and their corresponding polynucleotide sequences or (e.g. fragments of SEQ ID NO:1 and 3) are encompassed by the current invention, so long as the polypeptides retain some biological activity related to Su(var)2–10. A biological activity related to Su(var)2–10 includes for example, antigenicity or the ability to modulate heterochromatin gene expression or chromosome inheritance.

The polynucleotides and polypeptides of this invention were originally recovered from *Drosophila melanogaster*. Thus, the present invention provides means for isolating the nucleic acid molecules from other organisms, including humans, encoding the polypeptides of the present invention. For example, one may probe a gene library with a natural or artificially designed probe using art recognized procedures (see, for example: Current Protocols in Molecular Biology, Ausubel F. M. et al. (Eds.) Green Publishing Company Assoc. and John Wiley Interscience, New York, 1989, 1992). It is appreciated by one skilled in the art that probes can be designed based on the degeneracy of the genetic code to a sequences set forth in SEQ ID NO:2 and 4.

The invention includes polypeptides having substantially the same sequence as an amino acid sequence set forth in SEQ ID NO:2 or 4, or functional fragments thereof, or amino acid sequences that are substantially identical or the same as SEQ ID NO:2 or 4.

Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared.

When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol 48:443 (1970), by the search for similarity method of person & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

On example of a useful algorithm is BLAST and BLAST 2.0 algorithms, which are described in Altschul et al., Nuc. Acids Res. 25:3389–3402 (1977) and Altschul et al., J. Mol. Biol. 215:403–410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) or 11, an expectation (E) or 10, M=5, N=−4 and a comparison of both strands. For amino acid sequences, the BLASTP program uses as defaults a wordlength of 3, and expectations (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Natl. Acad. Sci. USA 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

A "substantially pure polypeptide" is typically pure when it is at least 60%, by weight, free from the proteins and naturally-occurring organic molecules with which it is naturally associated. Preferably, the preparation is at least 75%, more preferably at least 90%, and most preferably at least 99%, by weight, Su(var)2–10 polypeptide. A substantially pure Su(var)2–10 polypeptide may be obtained, for example, by extraction from a natural source (e.g., an insect cell); by expression of a recombinant nucleic acid encoding an Su(var)2–10 polypeptide; or by chemically synthesizing the protein. Purity can be measured by any appropriate method, e.g., by column chromatography, polyacrylamide gel electrophoresis, or by HPLC analysis.

Su(var)2–10 polypeptides of the present invention include peptides, or full length protein, that contains substitutions, deletions, or insertions into the protein backbone, that would still have an approximately 50%–70% homology to the original protein over the corresponding portion. A yet greater degree of departure from homology is allowed if like-amino acids, i.e. conservative amino acid substitutions, do not count as a change in the sequence. Polypeptide fragments of the invention retain a biological activity associated with Su(var)2–10 (e.g., antigenicity). For example, fragments containing epitopes of Su(var)2–10 are able to be identified by using Su(var)2–10 specific antibodies.

In addition to polypeptides of the invention, specifically disclosed herein is a DNA sequence for Su(var)2–10 represented by SEQ ID NO:1 and 3. DNA sequences of the invention can be obtained by several methods. For example, the DNA can be isolated using hybridization or computer-based techniques which are well known in the art. These include, but are not limited to: 1) hybridization of genomic libraries with probes to detect homologous nucleotide sequences; 2) antibody screening of expression libraries to detect cloned DNA fragments with shared structural features; 3) polyrnerase chain reaction (PCR) on genomic DNA using primers capable of annealing to the DNA sequence of interest; and 4) computer searches of sequence databases for similar sequences.

The polynucleotide encoding Su(var)2–10 includes a nucleotide sequence as set forth in SEQ ID NO:1 or 3, nucleic acid sequences complementary to a sequence set forth in SEQ ID NO:1 or 3, as well as splice variants thereof. When the sequence is RNA, the deoxyribonucleotides A, G, C, and T of SEQ ID NOs:1 and 3 are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes a polypeptide sequence as set forth in SEQ ID NO:2 or 4. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows:2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method of the invention embrace oligonucleotides of sufficient length and appropriate sequence which provides specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest.

Amplified products may be detected by Southern blot analysis, without using radioactive probes. In such a process, for example, a small sample of DNA containing a very low level of a Su(var)2–10 nucleotide sequence is amplified and analyzed via a Southern blotting technique known to those of skill in the art. The use of non-radioactive probes or labels is facilitated by the high level of the amplified signal.

Su(var)2–10 polynucleotide of the invention is derived from an insect (e.g., Drosophila). Screening procedures which rely on nucleic acid hybridization make it possible to isolate any gene sequence from any organism, provided the appropriate probe is available. For example, it is envisioned that such probes can be used to identify other homologs of the Su(var)2–10 family of factors in insects or, alternatively, in other organisms such as mammals, e.g., humans. In accomplishing this, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

When the entire sequence of amino acid residues of the desired polypeptide is not known, the direct synthesis of DNA sequences is not possible and the method of choice is use of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned.

DNA sequences encoding Su(var)2–10 can be expressed in vitro by DNA transfer into a suitable host cell, as described above.

In the invention, the Su(var)2–10 polynucleotide sequences may be inserted into a recombinant expression vector. The term "recombinant expression vector" refers to a plasmid, virus or other vehicle known in the art that has been manipulated by insertion or incorporation of the Su(var)2–10 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include those described above.

Polynucleotide sequences encoding Su(var)2–10 can be expressed in either prokaryotes or eukaryotes. Hosts can include microbial, yeast, insect and mammalian organisms. Such vectors are used to incorporate DNA sequences of the invention.

Methods which are well known to those skilled in the art can be used to construct expression vectors containing the Su(var)2–10 coding sequence and appropriate transcriptional/translational control signals. These methods include in vitro recombinant DNA techniques, synthetic techniques, and in vivo recombination/genetic techniques. (See, for example, the techniques described in Maniatis et al., 1989, Molecular Cloning A Laboratory Manual, Cold Spring Harbor Laboratory, N.Y.).

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method of producing a particular construct can easily be made by one skilled in the art based on practical considerations: size of the desired peptide, availability and cost of starting materials, etc. All the technologies involved are well established and well known in the art. See, for example, Ausubel et al., Current Protocols in Molecular Biology, Volumes 1 and 2 (1987), with supplements, and Maniatis et al., Molecular Cloning, a Laboratory Manual, Cold Spring Harbor Laboratory (1989). Yet other technical references are known and easily accessible to one skilled in the art.

Antibodies that Bind to Su(var)2–10

In another embodiment, the invention provides antibodies that bind to Su(var)2–10. Such antibodies are useful for research and diagnostics in the study of chromosomal inheritance, heterochromatin-associated gene expression, congenital disorders and birth defects, cell proliferative disorders (e.g., neoplasms, tumors) and Su(var)2–10-associated pathologies in general. A congenital disorder is a disorder existing at, and usually before, birth, regardless of its causation. Congenital disorders can be the result of a genetic change (e.g., a mutation or deletion of a gene), the result of infection (e.g., syphilis), the result of nutrition (e.g., a vitamin deficiency), or the result of exposure to an exogenous agent or toxin (e.g., thalidomide or an environmental toxicant), for example. Accordingly, the invention allows for the diagnosis in a subject of such congenital disorders associated with improper chromosomal inheritance. Such disorder can cause aneuploidy, which is associated with 45% of spontaneous abortions in humans (see, for example, Hyett J, Thilaganathan B First trimester screening for fetal abnormalities. Curr Opin Obstet Gynecol 1999 December;11(6):563–9; Harper J C, Wells D Recent advances and future developments in PGD. Prenat Diagn 1999 December;19(13):1193–9; Chitty L Prenatal screening for chromosome abnormalities. Br Med Bull 1998;54(4) :839–56; Evans M I, O'Brien J E, Johnson Screening for aneuploidy. Curr Opin Obstet Gynecol 1999 April;11(2) :115–8; and Munne and Cohen Chromosome abnormalities in human embryos. Hum Reprod Update 1998 November-December;4(6):842–55). Preferably the subject is a human.

Such antibodies may be administered alone or contained in a pharmaceutical composition comprising antibodies against Su(var)2–10 and other reagents effective as modulators chromosome inheritance, cell proliferative disorders and heterochromatin-associated gene expression both in vitro and in vivo.

The term "epitope", as used herein, refers to an antigenic determinant on an antigen, such as a Su(var)2–10 polypeptide, to which the paratope of an antibody, such as an Su(var)2–10-specific antibody, binds. Antigenic determinants usually consist of chemically active surface groupings of molecules, such as amino acids or sugar side chains, and can have specific three-dimensional structural characteristics, as well as specific charge characteristics.

Antibodies which bind to the Su(var)2–10 polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

An antibody suitable for binding to Su(var)2–10 is specific for at least one portion of a region of a Su(var)2–10 polypeptide, as shown in SEQ ID NO:2 and 4. For example, one of skill in the art can use a peptide to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in Immunochemical Protocols (Manson, ed.), pages 1–5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference.

The preparation of monoclonal antibodies likewise is conventional. See, for example, Kohler & Milstein, Nature, 256:495 (1975); Coligan et al., sections 2.5.1–2.6.7; and Harlow et al., Antibodies: A Laboratory Manual, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in Methods in Molecular Biology, Vol. 10, pages 79–104 (Humana Press 1992). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., Int. J. Cancer, 46:310 (1990), which are hereby incorporated by reference.

Alternatively, an anti-Su(var)2–10 antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA, 86:3833 (1989), which is hereby incorporated in its entirety by reference. Techniques for producing humanized monoclonal antibodies are described, for example, by Jones et al., Nature, 321: 522 (1986); Riechmann et al., Nature, 332: 323 (1988); Verhoeyen et al., Science, 239:1534 (1988); Carter et al., Proc. Nat'l Acad. Sci. USA, 89:4285 (1992); Sandhu, Crit. Rev. Biotech., 12:437 (1992); and Singer et al., J. Immunol., 150:2844 (1993), which are hereby incorporated by reference.

Antibodies of the invention also may be derived from human antibody fragments isolated from a combinatorial human immunoglobulin library. See, for example, Barbas et al., Methods: A Companion to Methods in Enzymology, Vol. 2, page 119 (1991); Winter et al., Ann. Rev. Immunol. 12: 433 (1994), which are hereby incorporated by reference. Cloning and expression vectors that are useful for producing a human immunoglobulin phage library can be obtained, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); and Taylor et al., Int. Immunol., 6:579 (1994), which are hereby incorporated by reference.

Antibody fragments of the invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and No. 4,331,647, and references contained therein. These patents are hereby incorporated in their entireties by reference. See also Nisonhoff et al., Arch. Biochem. Biophys,. 89:230 (1960); Porter, Biochem. J., 73:119 (1959); Edelman et al., Methods in Enzymology, Vol. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of VH and VL chains. This association may be noncovalent, as described in Inbar et al., Proc. Nat'l Acad. Sci. USA, 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Methods in Enzymology, Vol. 2, page 97 (1991); Bird et al., Science, 242:423 (1988); Ladner et al., U.S. Pat. No. 4,946,778; Pack et al., Bio/Technology, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology, Vol. 2, page 106 (1991).

Modulation of Chromosomal Inheritance and Heterochromatin Gene Expression

In one embodiment, the invention provides a method for modulating (e.g., inhibiting) chromosomal inheritance or heterochromatin-associated gene expression in a cell or a subject by administering to the cell or subject an effective amount of a composition which contains an Su(var)2–10 polypeptide, or biologically functional fragment thereof or an agent (e.g., an antibody, ribozyme, antisense molecule, or double-stranded interfering RNA molecules) that interacts with Su(var)2–10.

As used herein, an "effective amount" of a composition containing Su(var)2–10 or an Su(var)2–10-modulating agent is defined as that amount that is effective in modulating chromosomal inheritance or gene expression. For example, an inhibitory-effective amount would be that amount of the composition or agent sufficient to inhibit proper chromosomal inheritance or gene expression.

In another embodiment, the present invention provides a method for modulating Su(var)2–10 gene expression as well as methods for screening for agents which modulate Su(var) 2–10 gene expression. In this embodiment, a cell or subject is contacted with an agent suspected or known to have Su(var)2–10 gene expression modulating activity. The change in Su(var)2–10 gene expression is then measured as compared to a control or standard sample. The control or standard sample can be the baseline expression of the cell or subject prior to contact with the agent. An agent which modulates Su(var)2–10 gene expression may be a polynucleotide for example. The polynucleotide may be an antisense, a triplex agent, a ribozyme, or a double-stranded interfering RNA. For example, an antisense molecule may be directed to the structural gene region or to the promoter region of Su(var)2–10. The agent may be an agonist, antagonist, peptide, peptidomimetic, antibody, or chemical.

Double-stranded interfering RNA molecules are especially useful to inhibit expression of a target gene. For example, double-stranded RNA molecules can be injected into a target cell or organism to inhibit expression of a gene and the resultant gene products activity. It has been found that such double-stranded RNA molecules are more effective at inhibiting expression than either RNA strand alone. (Fire et al., Nature, 1998, 19:391(6669):806–11).

When a disorder is associated with abnormal expression of Su(var)2–10 (e.g., overexpression, or expression of a mutated form of the protein), a therapeutic approach which directly interferes with the translation of Su(var)2–10 messages into protein is possible. Alternatively, similar methodology may be used to study Su(var)2–10 gene activity. For example, antisense nucleic acid, double-stranded interfering RNA or ribozymes could be used to bind to the Su(var)2–10 mRNA or to cleave it. Antisense RNA or DNA molecules bind specifically with a targeted gene's RNA message, interrupting the expression of that gene's protein product. The antisense binds to the messenger RNA forming a double stranded molecule which cannot be translated by the cell. Antisense oligonucleotides of about 15–25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target Su(var)2–10-producing cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1:227, 1991; Helene, Anticancer Drug Design, 6:569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

These and other uses of antisense and ribozymes methods to inhibit the in vivo translation of genes are known in the art (e.g., De Mesmaeker, et al., Curr. Opin. Struct. Biol., 5:343, 1995; Gewirtz, A. M., et al., Proc. Natl. Acad. Sci. U.S.A., 93:3161, 1996b; Stein, C. A., Chem. and Biol. 3:319, 1996).

Delivery of antisense, triplex agents, ribozymes, competitive inhibitors, double-stranded interfering RNA and the like can be achieved using a recombinant expression vector such as a chimeric virus or a colloidal dispersion system or by injection. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number. of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

The agents useful in the method of the invention can be administered, for in vivo application, parenterally by injection or by gradual perfusion over time. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

Pharmaceutical Compositions

It is envisioned that the invention can be used to treat pathologies associated with cell proliferative disorders, chromosomal inheritance and Su(var)2–10 associated disorders. Therefore, the present invention encompasses methods for ameliorating a disorder associated with Su(var)2–10, including treating a subject having the disorder, at the site of the disorder, with an agent which modulates Su(var)2–10 activity. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of, an infection or disease in an invertebrate, a vertebrate, a mammal, particularly a human, and includes: (a) preventing the disease from occurring in a subject that may be predisposed to the disease, but has not yet been diagnosed as having it; (b) inhibiting the disease, i.e., arresting its development; or (c) relieving or ameliorating the disease, i.e., cause regression of the disease.

It is contemplated that administration of a Su(var)2–10 polypeptide, polynucleotides encoding Su(var)2–10 polypeptides, and polypeptides and polynucleotides encoding members of the protein family such as PIAS/ARIP3/Miz1 can be used to treat a Su(var)2–10 related disorder (e.g., cancer or chromosomal inheritance disorders).

Thus, the invention includes various pharmaceutical compositions useful for ameliorating symptoms attributable to a Su(var)2–10-associated disorder. The pharmaceutical compositions according to the invention are prepared by bringing an antibody against Su(var)2–10, a polypeptide or peptide derivative of Su(var)2–10, a Su(var)2–10 mimetic, a drug, chemical or combination of chemicals or a Su(var) 2–10-binding agent into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405–1412, 1461–1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249: 1527, (1990); Gilman et al. (eds.) (1 990), each of which is herein incorporated by reference.

In one embodiment, the invention provides a pharmaceutical composition useful for administering a Su(var)2–10 polypeptide, or nucleic acid encoding a Su(var)2–10 polypeptide, to a subject in need of such treatment. "Administering" the pharmaceutical composition of the present invention may be accomplished by any means known to the skilled artisan. Preferably a "subject" refers to a mammal, most preferably a human, but may be any organism.

The Su(var)2–10 protein or antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Screening Assay for Compounds That Affect Su (var)2–10

In another embodiment, the invention provides a method for identifying a compound which modulates Su(var)2–10 expression or activity including incubating components comprising the compound and a Su(var)2–10 polypeptide, or a recombinant cell expressing a Su(var)2–10 polypeptide, under conditions sufficient to allow the components to interact and determining the affect of the compound on the expression or activity of the gene or polypeptide, respectively. The term "affect", as used herein, encompasses any means by which Su(var)2–10 gene expression or protein activity can be modulated. Such compounds can include, for example, polypeptides, peptidomimetics, chemical compounds and biologic agents as described below.

Incubating includes conditions which allow contact between the test compound and Su(var)2–10, a cell expressing Su(var)2–10 or nucleic acid encoding Su(var)2–10. Contacting includes in solution and in solid phase. The test ligand(s)/compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008–1012, 1985), oligonucleotide ligation assays (OLAs) (Landegren, et al., Science, 241:1077, 1988), and the like. Molecular techniques for DNA analysis have been reviewed (Landegren, et al., Science, 242:229–237, 1988).

Thus, the method of the invention includes combinatorial chemistry methods for identifying chemical compounds that bind to Su(var)2–10 or affect Su(var)2–10 expression or activity. By providing for the production of large amounts of a Su(var)2–10, one can identify ligands or substrates that bind to, modulate, affect the expression of, or mimic the action of a Su(var)2–10. For example, a polypeptide may have biological activity associated with the wild-type protein, or may have a loss of function mutation due to a point mutation in the coding sequence, substitution, insertion, deletion and scanning mutations.

Areas of investigation are the development of therapeutic treatments. The screening identifies agents that provide modulation of Su(var)2–10 function in targeted organisms. Of particular interest are screening assays for agents that have a low toxicity for humans. A wide variety of assays may be used for this purpose, including labeled in vitro protein-protein binding assays, protein-DNA binding assays, electrophoretic mobility shift assays, immunoassays for protein binding, and the like. The purified protein may also be used for determination of three-dimensional crystal structure, which can be used for modeling intermolecular interactions, for example.

The term "agent" as used herein describes any molecule, e.g. protein or pharmaceutical, with the capability of altering or mimicking the physiological function or expression of Su(var)2–10. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrmidines, derivatives, structural analogs or combinations thereof Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification and amidification to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors and anti-microbial agents may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

In addition, cells or organisms which have a mutation in a Su(var)2–10 sequence may be used as models to screen for agents which modulate disorders associated with the mutation. For example, the inventors have identified that organisms (e.g., Drosophila) which lack normal Su(var)2–10 activity demonstrate a lethal phenotype. Accordingly, administration of agents to organism having such a mutation, or cells derived or recombinantly modified to have a reduced Su(var)2–10 activity may be used to determine the effect of the drug or agent on neurodegeneration.

Detection of Su(var)2–10 in Vivo and in Vitro

In a further embodiment, the invention provides a method of detecting Su(var)2–10 or diagnosing a Su(var)2–10-associated disorder in a subject including contacting a cell component containing Su(var)2–10 with a reagent which binds to the cell component. The cell component can be or contain a nucleic acid, such as DNA or RNA, or a protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation.

In addition, the antibodies, polypeptides and polynucleotide sequences of the invention can be used to diagnosis a Su(var)2–10 associated disorder. As described more fully below, Su(var)2–10 can be characterized as modulating gene transcription due to the effects on heterochromatin formation. Su(var)2–10 is closely related to the PIAS/ARIP3/Miz1 protein family, a highly conserved group with diverse functions. Detection of mutations in this family of proteins (e.g., mutations in Su(var)2–10, PIAS, ARIP3 or Miz1) can be used to diagnose disorders associated with cell proliferation (e.g. cancer), which may be linked to improper chromosomal inheritance or gene expression resulting from improper heterochromatin regulation. Accordingly, methods of detection of Su(var)2–10 or related members of the conserved family can be used to diagnose cell proliferative disorders and congenital defects. Such methods contemplate the use of antibodies to- and polynucleotides encoding-members of this protein family. Although, Su(var)2–10 is exemplified herein, the diagnostic methods and compositions are applicable to Su(var)2–10 as well as PIAS, ARIP3, Miz1, and other members of this family.

Antibodies useful in the diagnosis of cell proliferative disorders should preferably bind to a mutant protein and not the wild type protein. Monoclonal antibodies that bind to mutant proteins can be generated utilizing a fragment or peptide including the mutant sequence. Such antibodies can be used in immunoassays such as competitive and noncompetitive immunoassays in either a direct or indirect format. Examples of such immunoassays are the radioimmunoassay (RIA), the sandwich (immunometric assay) and the Western blot assay.

Similarly, polynucleotide sequences that specifically hybridize to mutant and not wild-type nucleic acid sequences of interest can be used to identify mutant nucleic acid sequences encoding members of the PIAS/ARIP3/Miz1/Su(var)2–10 protein family. Techniques for labeling and detecting mutant polynucleotide sequence are known in the art and include, for example, northern blots, southern blots, and PCR.

For purposes of the invention, an antibody or nucleic acid probe specific, for example, to a Su(var)2–10 polypeptide, polynucleotide or fragments thereof, may be used to detect the presence of Su(var)2–10 polypeptide (using antibody) or polynucleotide (using nucleic acid probe) in biological fluids or tissues. Any specimen containing a detectable amount of Su(var)2–10 antigen or polynucleotide can be used. In addition, antibodies and polynucleotides designed to recognize mutations in a Su(var)2–10 polypeptide or polynucleotide may be used. Specimens include, for example, blood, urine, cerebrospinal fluid, synovial fluid or any tissue.

Another technique which may also result in greater sensitivity consists of coupling antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific antihapten antibodies.

Alternatively, a Su(var)2–10 polypeptide can be used to detect antibodies to Su(var)2–10 polypeptide in a specimen. Any of the Su(var)2–10 polypeptides of the invention is suited for use in immunoassays in which it can be utilized in liquid phase or bound to a solid phase carrier. In addition, a Su(var)2–10 used in these assays can be detectably labeled in various ways.

Examples of immunoassays which can utilize the Su(var)2–10 of the invention are competitive and noncompetitive immunoassays in either a direct or indirect format. Examples of such immunoassays are the radioimmunoassay (RIA), the sandwich (immunometric assay) and the Western blot assay. Detection of antibodies which bind to a Su(var)2–10 of the invention can be done utilizing immunoassays which run in either the forward, reverse, or simultaneous modes, including immunohistochemical assays on physiological samples. The concentration of Su(var)2–10 which is used will vary depending on the type of immunoassay and nature of the detectable label which is used. However, regardless of the type of immunoassay which is used, the concentration of Su(var)2–10 utilized can be readily determined by one of ordinary skill in the art using routine experimentation.

A Su(var)2–10 of the invention can be bound to many different carriers and used to detect the presence of antibody specifically reactive with the polypeptide. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding Su(var)2–10 or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

For purposes of the invention, an antibody which binds to a Su(var)2–10 of the invention may be present in various biological fluids and tissues. Any sample containing a detectable amount of antibodies to Su(var)2–10 can be used. Typically, a sample is a liquid such as urine, saliva, cerebrospinal fluid, blood, serum and the like, or a solid or semi-solid such as tissue, feces and the like.

A monoclonal antibody of the invention, directed toward Su(var)2–10, is useful for the in vivo and in vitro detection of antigen. The detectably labeled monoclonal antibody is given in a dose which is diagnostically effective. The term "diagnostically effective" means that the amount of detectably labeled monoclonal antibody is administered in sufficient quantity to enable detection of Su(var)2–10 antigen for which the monoclonal antibodies are specific.

The concentration of a detectably labeled monoclonal antibody administered to a subject should be sufficient such that the binding to those cells, body fluid, or tissue having Su(var)2–10 is detectable compared to the background. Further, it is desirable that the detectably labeled monoclonal antibody be rapidly cleared from the circulatory system in order to give the best target-to-background signal ratio.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 key range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of a Su(var)2–10-associated disorder. Thus, by measuring the increase or decrease of Su(var)2–10 polypeptide present in various body fluids or tissues, it would be possible to determine whether a particular therapeutic regiment aimed at ameliorating the disorder is effective.

In another embodiment, nucleic acid probes can be used to identify Su(var)2–10 nucleic acid from a specimen obtained from a subject. Examples of specimens from which nucleic acid sequence encoding Su(var)2–10 can be derived include insect, human, swine, porcine, feline, canine, equine, murine, cervine, caprine, lupine, leporidine and bovine species.

Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res. 9:879, 1981).

In an embodiment of the invention, purified nucleic acid fragments containing intervening sequences or oligonucleotide sequences of 10–50 base pairs are radioactively labeled. The labeled preparations are used to probe nucleic acids from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see Genetic Engineering, 1, ed. Robert Williamson, Academic Press, (1981), 72–81). Alternatively, nucleic acid from the specimen can be bound directly to filters to which the radioactive probe selectively attaches by binding nucleic acids having the sequence of interest. Specific sequences and the degree of binding is quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

For the most part, the probe will be detectably labeled with an atom or inorganic radical, most commonly using radionuclides, but also heavy metals can be used. Conveniently, a radioactive label may be employed. Radioactive labels include $^{32}P$, $^{125}I$, $^{3}H$, $^{14}C$, $^{111}In$, $^{99}Tc$, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization.

The manner in which the label is bound to the probe will vary depending upon the nature of the label. For a radioactive label, a wide variety of techniques can be employed. Commonly employed is nick translation with an a $^{32}P$-dNTP or terminal phosphate hydrolysis with alkaline phosphatase followed by labeling with radioactive $^{32}P$ employing $^{32}P$-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified, with inorganic acids, e.g., $^{32}P$ phosphate, or $1^{14}C$ organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

Standard hybridization techniques for detecting a nucleic acid sequence are known in the art. The particular hybridization technique is not essential to the invention. Other hybridization techniques are described by Gall and Pardue, (Proc. Natl. Acad. Sci. 63:378, 1969); and John, et al., (Nature, 223:582, 1969). As improvements are made in hybridization techniques they can readily be applied in the method of the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

Transgenic Organisms

The present invention also contemplates transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a published procedure by Love et al., (Biotechnology, Jan. 12, 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include, for example, bovine, porcine, ovine and avian animals (e.g., cow, pig, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., Proc. Natl. Acad. Sci. USA 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal which includes exogenous genetic material within all of its cells. A "transgenic" animal can be produced by cross-breeding two chimeric animals which include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken -globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927–6931, 1985; Van der Putten, et al., Proc. Natl. Acad. Sci USA 82:6148–6152, 1985). Transfection is easily and efficiently obtained by culturing the blastomeres on a monolayer of virus-producing cells (Van der Putten, supra; Stewart, et al., EMBO J. 6:383–388, 1987). Alternatively, infection can be performed at a later stage. Virus or virus-producing cells can be injected into the blastocoele (D. Jahner et al., Nature 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154–156, 198 1; M. O. Bradley et al., Nature 309: 255–258, 1984; Gossler, et al., Proc. Natl. Acad. Sci USA 83: 9065–9069, 1986; and Robertson et al., Nature 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extrachromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences which encode Su(var)2–10, and include Su(var) 2–10-sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout(i.e., knockout of Su(var) 2–10thetase). The term "gene knockout" as used herein, refers to the targeted disruption of a gene in vivo with complete or partial loss of function that has been achieved by any transgenic technology familiar to those in the art (e.g., insertion of a P-element in Drosophila). In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

In one embodiment, the transgene comprises DNA antisense to the coding sequence for Su(var)2–10. In another embodiment, the transgene comprises DNA encoding an antibody which is able to bind to Su(var)2–10. Where appropriate, DNA sequences that encode proteins having Su(var)2–10 activity but differ in nucleic acid sequence due to the degeneracy of the genetic code may also be used herein, as may truncated forms, allelic variants and interspecies homologues.

The invention also includes animals having heterozygous mutations in Su(var)2–10 or partial inhibition of Su(var) 2–10 function or expression. One of skill in the art would readily be able to determine if a particular mutation or if an antisense molecule was able to partially inhibit Su(var)2–10. For example, in vitro testing may be desirable initially by comparison with wild-type or untreated Su(var)2–10 (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals endogenous Su(var)2–10 gene(s), a marker gene fragment can be included in the construct in the 3' untranslated region of the transgene and the Northern probe designed to probe for the marker gene fragment. The serum levels of Su(var)2–10 can also be measured in the transgenic animal to establish appropriate expression. Expression of the Su(var)2–10 transgenes, thereby decreasing the Su(var)2–10 in the tissue and serum levels of the transgenic animals.

Transgenic organisms of the invention are highly useful in the production of organisms for study of tumorgenesis and in identifying agents or drugs with inhibit or modulate tumorgenesis and inheritance.

It will be recognized that the method of creating a transgenic organism include methods of inserting a transgene into, for example, an embryo of an already created transgenic organism, the organism being transgenic for a different unrelated gene or gene product.

In one embodiment the transgenic organism is an insect. An insect as used herein denotes all insect species. Typically the insect is selected from the group consisting of bristletails, springtails, mayflies, dragonflies, damselflies, grasshoppers, crickets, walkingstickes, praying-mantises, cockroaches, earwigs, termites, stoneflies, lice, thrips, bed bugs, plant bugs, damsel bugs, flower bugs, assassin bugs, ambush bugs, lace bugs, stink bugs, cicadas, treehoppers, leafhoppers, spittlebugs, planthoppers, aphids, whiteflies, beetles, scropionflies, caddisflies, moths, skippers, butterflies, crane flies, sand flies, mosquitoes, horse flies; fruit flies louse flies, bees, wasps, and ants.

The transgenic insects of the invention can be produced by introducing into single cell embryos DNA disrupting expression of a nucleic acid encoding the wild type Su(var) 2–10 sequence. Transgenic insects can be generated by microinjection, which can produce P-element mediated germ line transformation. For transgenic insects, generally the transgene is introduced at an embryonic stage. For example, transgenic insects of the present invention can be produced by introducing into single cell embryos invention polynucleotides, either naked or contained in an appropriate vector, by microinjection, for example, which can produce insects by P-element mediated germ line transformation (see e.g., Rubin et al., *Science* 218:348–353 (1982)). Totipotent or pluripotent stem cells transformed by microinjection, calcium phosphate mediated precipitation, liposome fusion, retroviral infection or other means are then introduced into the embryo, and the polynucleotides are stably integrated into the genome. A transgenic embryo so transformed then develops into a mature transgenic insect in which the transgene is inherited in normal Mendelian fashion. Additional methods for producing transgenic insects can be found, for example, in O'Brochta et al., *Insect Biochem. Mol. Biol.* 26:739–753 (1996) and in Louleris et al., *Science* 270:2002–2005 (1995).

In a one method, developing insect embryos are infected with a virus, such as a baculovirus (e.g., Autographa californica AcNPV), containing the desired invention polynucleotide, and transgenic insects produced from the infected embryo. The virus can be an occluded virus or a nonoccluded virus. A virus can be occluded by coinfection of cells with a helper virus which supplies polyhedrin gene function. The skilled artisan will understand how to construct recombinant viruses in which the polynucleotide is inserted into a nonessential region of the baculovirus genome. For example, in the AcNPV genome, nonessential regions include the p 10 region (Adan et al., *Virology* 444:782–793, 1982), the DA26 region (O'Reily et al., *J. Gen. Virol.* 71:1029–1037, 1990), the ETL region (Crawford et al., *Virology* 62:2773–2781, 1988), the egt region (O'Reily et al., *J. Gen. Virol.* 64:1321–1328), amongst others. Significant homology exists among particular genes of different baculoviruses and therefore, one of skill in the art will understand how to insert an invention polynucleotide into similar nonessential regions of other baculoviruses. Thus, for example, a sequence encoding a Su(var)2–10 polypeptide as set forth in SEQ ID NO:2 or 4 may be placed under control of an AcNPV promoter (e.g., the polyhedrin promoter). Depending on the vector utilized, any of a number of suitable transcription and translation elements, including constitutive, inducible and conditional promoters, enhancers, transcription terminators, etc. may be used in order to transcribe invention polynucleotides or express invention polypeptides. Alternatively, a transgene containing a nucleic acid sequence disrupting expression of Su(var) 2–10 may not contain a promoter as the nucleic acid sequence need not be transcribed or translated to obtain a transgenic insect having disrupted Su(var)2–10.

Thus, the invention provides methods for producing transgenic insects having a disrupted nucleic acid sequence encoding Su(var)2–10. The methods include introducing into the genome of an insect a nucleic acid construct, including a disrupted or mutated Su(var)2–10 gene, and obtaining a transgenic insect having a disrupted nucleic acid sequence encoding Su(var)2–10. The invention further provides methods for producing transgenic insects having a nucleic acid encoding Su(var)2–10 polypeptide or functional fragment thereof Insecticidal Compositions The invention further provides insecticidal compositions. In one embodiment, a transgenic insect carrying a transgene comprising DNA disrupting expression of a nucleic acid encoding an Su(var)2–10 polypeptide (e.g., SEQ ID NO:2), in a manner such that these polynucleotides are stably integrated into the DNA of germ line cells of the mature insect and inherited in normal Mendelian fashion, is released into the environment. The insect can then mate with insects in the environment, such that the progeny will carry DNA disrupting expression of a nucleic acid sequence encoding a Su(var)2–10 polypeptide. After tow or more generations of mating of the transgenic insects with the insects in the environment, progeny insects will be produced which are homozygous for the transgene. In one embodiment, these progeny will have disrupted chromosome inheritance resulting in death.

In another embodiment, a genetically engineered viral vector of the invention can be used as a component of agricultural compositions for applying to plants, plant environments, or distributed in baits to effect the biological control of insect pests. The target insect guides one of skill in the art in the selection of the agent for insect control.

The concentration of the insecticide that will be required to produce insecticidally effective compositions will depend on the type of organism targeted and the formulation of the composition. By "insecticidally effective" means an amount sufficient to cause a significant reduction in an insect population. The insecticidally effective concentration can readily be determined experimentally by one of skill in the art. Agricultural compositions for control of insect pests or plants should be suitable for agricultural use and dispersal in fields. Reviews describing methods of application of biological insect control agents and: methods and compositions for agricultural application are available. See, for example, Couch and Ignoffo, In: Microbial Control of Pests and Plant Disease 1970–1980, Burges (ed.), Chapter 34, pp. 621–634, 1981; Corke and Rishbet, ibid, Chapter 39, pp. 717–732; Brockwell, In: Methods for Evaluating Nitrogen Fixation, Bergersen (ed.), pp. 417–488, 1980; Burton, In: Biological Nitrogen Fixation Technology for Topical Agriculture, Graham and Harris (eds.), pp. 105–114, 1982; Roghley, ibid, pp. 115, 127, 1982; and The Biology of Baculoviruses, Vol. II, Biological Properties and Molecular Biology, CRC Press, Inc. Boca Raton, Fla., 1986.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLES

Loci altering heterochromatin-induced gene silencing may encode chromosomal proteins that control heterochromatin metabolism. In Drosophila 100 or more loci modify PEV in trans (Suppressors and Enhancers of PEV, or Su(var)s and E(var)s). The gene products and functions of cloned modifier loci indicate that some of these genes are required for normal chromosome functions, including DNA replication and transcriptional regulation (reviewed in (Wallrath, L. L. (1998), Curr Opin Genet Dev 8, 147–53)).

A trio of genes (Swi6, Clr4, Rik1) were originally identified as mutations which alleviated genomic silencing; subsequently, they were shown to encode centromere-associated proteins that control chromosome inheritance (Allshire, R. C., et al. (1995), Genes Dev 9, 218–33). In Drosophila, a small number of PEV modifiers have been linked to chromosome inheritance functions (Bhat et al., (1996), Development 122, 1113–24; Fanti et al. (1998), Mol Cell 2, 527–38; Kellum, R., and Alberts, B. M. (1995), J Cell Sci 108, 1419–31; Wines, D. R., and Henikoff, S. (1992), Genetics 131, 683–91). For example, the HP1 protein (encoded by Su(var)205) promotes accurate chromosome segregation in embryos and is required to prevent chromosome fusions in diploid cells (Fanti et al. (1998), Mol Cell 2, 527–38; Kellum, R., and Alberts, B. M. (1995), J Cell Sci 108, 1419–31). Interestingly, mammalian homologs of the Drosophila SU(VAR)3–9 protein have recently been shown to bind centromeric regions on human metaphase chromosomes (Aagaard, L. et al. (1999), Embo J 18, 1923–38).

Su(var)2–10 Mutations Cause Dominant Reductions in Sensitized Minichromosome Transmission Su(var)2–10 was identified as a candidate chromosome inheritance locus in a screen for dominant Su(var) effects on the transmission of a sensitized Dp1187 minichromosome derivative, J21A. J21A (FIG. 1) lacks one-third of the 420 kb region required for full centromere function and shows reduced monosome transmission from parents to progeny (27%), in comparison to the normal 50% monosome transmission of minichromosome derivatives that contain an intact centromere (Murphy, T. D., and Karpen, G. H. (1995), Cell 81, 139–48). Two independently isolated alleles of Su(var)2–10 (Su(var)2–10$^1$ and Su(var)2–10$^2$, Wustmann et al. (1989), Mol Gen Genet 217, 520–7) dramatically decreased J21A transmission.

Su(var)2–10 mutations exhibited two intriguing interactions with Dp1187 deletion derivatives. First, Su(var)2–10$^1$ and Su(var)2–10$^2$ caused both zygotic and maternal reductions in J21A transmission. As shown in Table 1, Su(var)2–10 mutations exhibited weak but reproducible decreases in J21A transmission when the mutant chromosome was inherited from the father (left column, without transgene, rows 3 and 5). When the Su(var)2–10$^1$ and Su(var)2–10$^2$ chromosomes were inherited from the mother, zygotic and maternal defects combined to reduce J21A transmission levels to 7% and 8%, respectively (left column, without transgene, rows 2 and 4). These data indicate that Su(var)2–10 is required early in development when maternal RNAs are being transcribed, and also later in development. Increasing the dose of Su(var)2–10+ using a transgene (right column, with transgene, row 1; see below) also reduced J21A transmission, indicating that cells are quite sensitive to increases in Su(var)2–10 product. Interestingly, deficiencies that remove Su(var)2–10 had no apparent effect on J21A transmission, suggesting that Su(var)2–10$^1$ and Su(var)2–10$^2$ may encode misexpressed or abnormal proteins that interfere with chromosome transmission.

Secondly, both Su(var)2–10$^1$ and Su(var)2–10$^2$ displayed centromere-specific interaction patterns when tested against a panel of Dp1187 minichromosome derivatives. Derivatives with partially functional centromeres (IB, 25A, J21A) were further destabilized by heterozygosity for Su(var)2–10$^1$ and Su(var)2–10$^2$. The transmission rates of derivatives with fully functional centromeres (γ238, 20A, 3A, 31E2, 10B) remained unchanged. In contrast, a heterozygous nod mutation destabilized the transmission of Dp1187 derivatives that are deleted for extracentromeric DNA. NOD is a chromokinesin that binds all along chromosome arms (Afshar, K. et al. (1995), Cell 81, 129–38) and sequences distributed throughout the chromosome are required for its function in normal chromosome inheritance (Murphy, T. D., and Karpen, G. H. (1995), Cell 81, 139–48). The centromere-specific pattern of Su(var)2–10 interactions is typical of proteins which require only the centromeric region for their chromosome inheritance roles (Cook et al. (1997), Genetics 145, 737–47).

Su(var)2–10 is Essential for the Normal Inheritance of Endogenous Chromosomes

Su(var)2–10 homozygotes are inviable demonstrating that Su(var)2–10 is an essential gene. Data from deficiency mapping and lethality rescue experiments indicated that additional lethal mutations exist along the Su(var)2–10$^1$ and Su(var)2–10$^2$ chromosomes. To determine when Su(var)2–10 mutants die, the development of Su(var)2–10$^1$/Su(var)2–10$^2$ and Su(var)2–10$^2$/Su(var)2–10$^{Pex74a}$ trans-heterozygous animals (for a description of Su(var)2–10$^{Pex74a}$, a deletion of the locus, see below and FIG. 2B) was examined. These mutants exhibited a late larval to early pupal lethal phase, and 3–15% of Su(var)2–10$^1$/Su(var)2–10$^2$ larvae had melanotic tumors.

To determine if the strong dominant effects exerted by Su(var)2–10 mutations on sensitized minichromosome inheritance and the recessive lethality reflect a general requirement for Su(var)2–10 in the inheritance of all chromosomes, or is the effect minichromosome-specific, the late lethal phase of Su(var)2–10 trans-heterozygotes was examiner. This trans-heterozygote allowed us to address this question using mitotically-active neuroblast tissue from mutant third-instar larvae. Balancer chromosomes expressing Green Fluorescent Protein were used to distinguish Su(var)2–10$^1$/Su(var)2–10$^2$ from Su(var)2–10/Balancer larvae (Casso et al. (1999), Mech Dev 88, 229–232). The mitotic index of Su(var)2–10 mutant neuroblasts was significantly higher than in wild-type, suggesting that mutant cells were delayed or arrested in mitosis. The structure and function of endogenous chromosomes in Su(var)2–10 mutants was grossly abnormal. Su(var)2–10$^1$/Su(var)2–10$^2$ larval neuroblasts exhibited two major types of chromosomal defects: hypocondensed chromosomes in metaphase and aberrantly segregating chromosomes in anaphase. The hypocondensation of metaphase chromosomes may represent an extreme version of the chromatin unwinding that could cause the dominant PEV phenotype in Su(var)2–10 heterozygotes. Anaphase segregation defects included chromosome fragmentation and chromosome bridging. The severe defects in endogenous chromosome inheritance are consistent with the J21A minichromosome response to Su(var)2–10 heterozygosity.

The penetrance of the mitotic defects was temperature sensitive (Table 2). The percentage of mutant larvae with melanotic tumors increased with temperature (from 15% at 25° C. to 63% at 28° C.), and the most severe mitotic defects observed at 25° C. occurred in tumor-bearing larvae. Using a liberal definition for hypocondensation (to guard against scoring bias, see Experimental Procedures) we found a slight increase in the percentage of hypocondensed metaphases in wild type versus mutant at 25° C. (22% to 35%, respectively), but a very large increase at 28° C. (18% versus 61%). Anaphase segregation defects were more common in Su(var)2–10 mutants than in wild type, but did not show pronounced temperature sensitivity (18% at 25° C. and 19% at 28° C.). Only 2% of anaphase figures from wild type controls were aberrant at either temperature. The significantly elevated frequencies of mitotic defects and the recessive lethality displayed by homozygous mutants demonstrate that Su(var)2–10 is essential for the normal inheritance of all chromosomes, not just sensitized minichromosomes.

Su(var)2–10 Mutations Alter Polytene Chromosome Structure and Nuclear Organization Many tissues of Drosophila melanogaster third instar larvae contain polytene nuclei. These interphase nuclei undergo multiple rounds of DNA replication without mitotic division, yielding large chromosomes that are amenable to high resolution cytological analyses. To determine whether Su(var)2–10 controls general aspects of chromosome architecture, polytene chromsome structure was analyzed in whole mount salivary gland nuclei from wild type and Su(var)2–10$^2$/Su(var)2–10$^{Pex74a}$ third instar larvae. Similar results were obtained for Su(var)2–10$^1$/Su(var)2–10$^2$ larvae, although the penetrance and severity of the phenotypes was less pronounced. Salivary glands from mutants were dramatically reduced in size, and nuclei throughout the tissue were disorganized. The consistent banding pattern of normal polytene chromosomes was completely absent in Su(var)2–10 mutant chromosomes. The chromosomes were disorganized within the nuclei and appeared to be undercondensed, consistent with the hypocondensation of diploid metaphase chromosomes described above. In addition, the small size of the chromosomes and nuclei relative to their temporal stage of development suggests a defect in endoreplication. These chromosome structure defects are not simply a result of the reduced nuclear size since comparably sized nuclei from younger wild type larvae exhibited normal polytene chromosome structure. These results demonstrate that Su(var)2–10 controls chromosome structure in both polytene and diploid cells, and that its function in polytene cells either establishes or maintains the nuclear organization of chromosomes.

Molecular Characterization of Su(var)2–10

As a first step towards cloning the locus, its location was refined by deficiency mapping the lethal phenotype to polytene region 45A. Complementation test were then performed on a collection of P-element-induced lethal mutations localized to this area by the Berkeley Drosophila Genome Project (BDGP). One insertion, P{PZ}1(2)03697$^{03697}$, failed to complement Su(var)2–10$^1$ and Su(var)2–10$^2$ for lethality, suggesting that this insertion is an allele of Su(var)2–10. P{PZ}1(2)03697$^{03697}$ was recently reported to be inserted into the Zimp (zinc finger-containing, Miz1, PIAS3-like) transcription unit (Mohr, S. E., and Boswell, R. E. (1999), Gene 229, 109–16), named for its predicted homology to other proteins, and without knowledge of allelism to Su(var)2–10. The genetically-based Su(var)2–10 nomenclature is used due to historical precedence (Wustmann et al (1989), Mol Gen Genet 217, 520–7). Precise excisions of P{PZ}1(2)03697$^{03697}$ reverted the lethal phenotype of the P insertion and complemented both Su(var)2–10 EMS alleles for lethality. These data demonstrate that P{PZ}1(2)03697$^{03697}$ is a bona fide allele of Su(var)2–10, which is now referred to as Su(var)2–10$^{03697}$.

Figure 2:
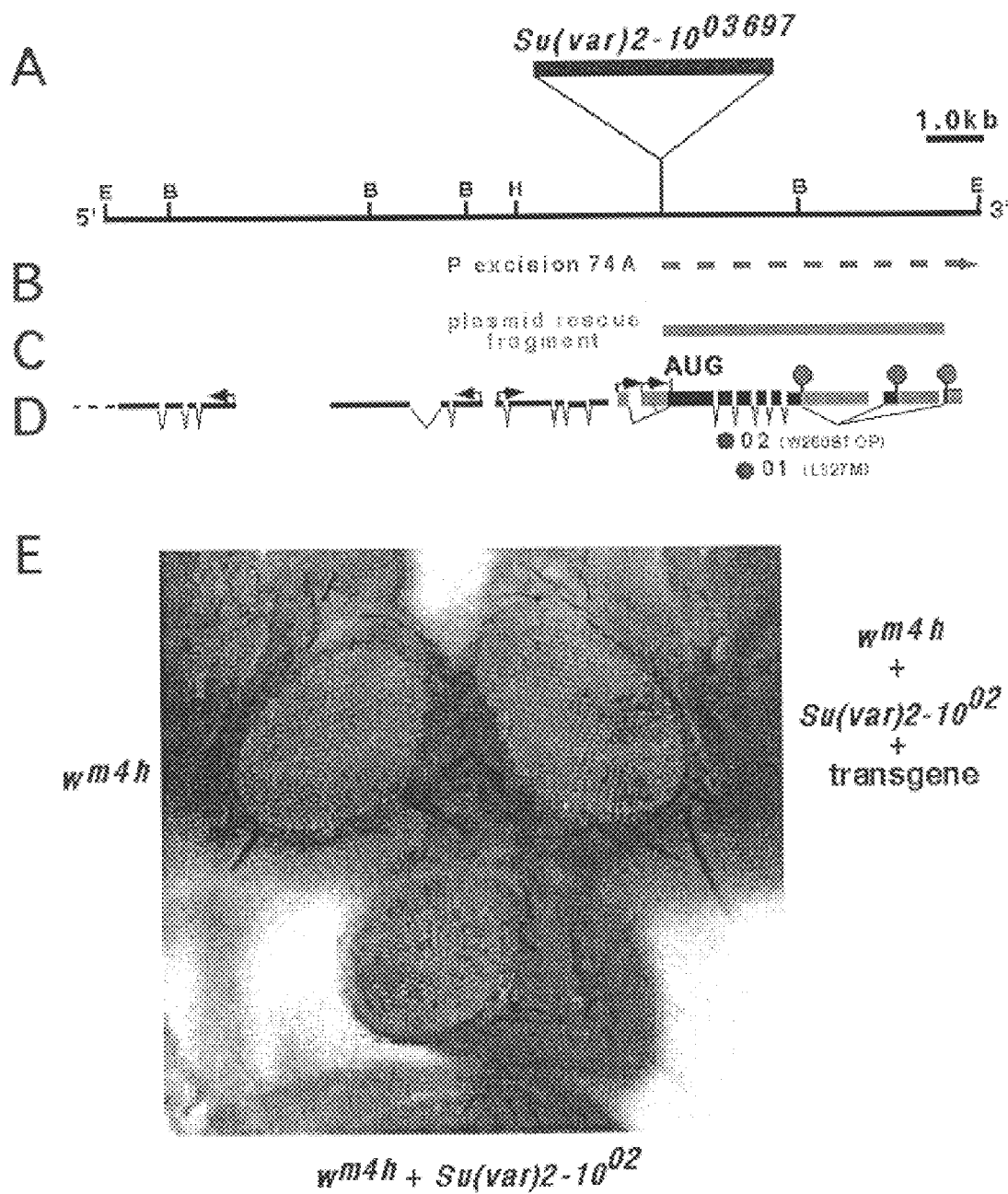

The molecular characterization of this region is presented in FIG. 2, and the predicted Su(var)2–10 transcript is indicated with light gray bars (FIG. 2D). Four observations demonstrate that Su(var)2–10 is encoded by this transcript. First, the Su(var)2–10$^{03697}$ P element is inserted into the second exon of this transcription unit. Second, imprecise P excision alleles that created deletions to the left of the insertion complemented Su(var)2–10 mutations for lethality, whereas deletions to the right that removed the transcription unit did not (e.g. Pex74a, FIG. 2B). Third, the Su(var)2–10$^1$ and Su(var)2–10$^2$ mutations contain single base changes within the coding region of the same transcript disrupted by the Su(var)2–10$^{03697}$ insertion (FIG. 2D). A T->A change at the first position of the codon for amino acid 327 yields a leucine to methionine mutation in the Su(var)2–10$^1$ allele. In the Su(var)2–10$^2$ allele, a G->A change at the third position of the codon for amino acid 260 yields a tryptophan to STOP mutation, which is predicted to eliminate the carboxyl half of the protein. Fourth, a 15 kb genomic transgene containing the putative Su(var)2–10 locus (FIG. 2A) rescued the lethal phenotype of Su(var)2–10$^{03697}$ homozygotes and Su(var)2–10$^1$/Su(var)2–10$^2$ trans-heterozygotes. This transgene also rescued the dominant suppression of PEV phenotype of both EMS alleles (FIG. 2E), and the dominant minichromosome inheritance defects of Su(var)2–10$^2$ (Table 1, rows 4 and 5). While the zygotic reduction in J21A transmission was rescued for Su(var)2–10$^1$ (Table 1, row 3), the maternal effects caused by this mutation were not restored (Table 1, row 2), suggesting that this allele may have novel, dominant effects on the maternal contribution of Su(var)2–10. Based on the behavior of Su(var)2–10$^{03697}$ P element excisions, the DNA sequence changes in both EMS alleles of Su(var)2–10, and the ability of the 15 kb transgene to rescue multiple Su(var)2–10 mutant phenotypes, we conclude that we have cloned Su(var)2–10.

TABLE 1

J21A Minichromsome Transmission Rates in Su(var)2-10 Heterozygotes

| Genotype | 31 transgene (% ± σ) | +transgene (% ± σ) |
|---|---|---|
| +/+ | 27 ± 12 | 14 ± 9 |
| Su(var)2-10$^1$/+ | 7 ± 5 | 10 ± 7 |
| Su(var)2-10$^1$ +[b] | 20 ± 10 | 30 ± 13 |
| Su(var)2-10$^2$/+ | 8 ± | 23 ± 8 |
| Su(var)2-10$^2$/+[b] | 16 ± 9 | 25 ± 14 |

Monosome transmission for the J21A minichromsome from individual females of the indicated genotype was measured as described, and the average percent transmission±SD(s) is shown. [a]The transgene construct is described and illustrated in FIG. 2. [b]Mutation chromosome inherited from the father, revealing only the zygotic defects caused by the mutation.

TABLE 2

Endogenous Chromsome Defects in Su(var)2-10 Mutants

|  | +/+ 25° C. | +/+ 28° C. | Su(var)2-10$^1$/Su(var)2-10$^2$ 25° C. | Su(var)2-10$^1$/Su(var)2-10$^2$ 28° C. |
|---|---|---|---|---|
| mitotic index | 1.04 | 1.01 | 1.39 | 1.26 |
| under-condensed metaphases (%) | 22 | 18 | 35 | 61 |
| aberrant anaphases (%) | 2 | 2 | 18 | 19 |

The mitotic index, percentage of undercondensed metaphases and percentage of aberrant anaphases is shown for the indicted genotypes at 25° C. and 28° C. The number of brains scored for each data set was the following: +/+ at 25° C.=9; +/+ at 28° C.=5 Su(var)2-10$^1$/Su(var)2-10$^2$ at 25° C.=13; and Su(var)2-10$^1$/Su(var)2-10$^2$ at 28° C.=8.

Northern blot and RNA in situ analyses indicate that Su(var)2-10 mRNA is heavily loaded by mothers into eggs. These data are consistent with the maternal effects of Su(var)2-10 mutations on minichromosome inheritance and the late stage of lethality displayed by trans-heterozygous mutants. Multiple Su(var)2-10 transcripts are found in embryos, larvae, and adult females. Transcript sizes of the most prevalent forms at these developmental stages are 2.1 kb, 2.4 kb and 4.4 kb, consistent with the predicted sizes of transcripts deduced from cDNA and EST analysis. Adult males express a single 2.3 kb transcript, demonstrating that the regulation of Su(var)2-10 is different in adult males and females.

SU(VAR)2-10 is a Member of the PIAS/ARIP3/Miz1 Protein Family

Conceptual translation of Su(var)2-10 ORFs yields four predicted protein products (522aa, 537aa, 554aa and 593aa). SU(VAR)2-10 is homologous to a diverse group of proteins which includes members of the recently identified Protein Inhibitor of Activated STAT (PIAS) family, the testis-specific Androgen Receptor Interacting Protein (ARIP3) from mice and the Msx-Interacting Zinc-finger protein (Miz1), also from mice (Chung et al. (1997), Science 278, 1803–5; Liu et al. (1998), Proc Natl Acad Sci USA 95, 10626–31; Moilanen et al. (1999), J Biol Chem 274, 3700–4; Wu et al. (1997), Mech Dev 65, 3–17). The orthologs and their various functions are outlined in Table 3, as is the percentage of sequence identity and similarity over a 301aa stretch wherein the homology is highest. This central region of SU(VAR)2-10 is 50–57% identical and 72–82% similar to the corresponding domain of the orthologous proteins, and represents over half of the total protein. The percent identity/similarity decreases in the N- and C-terminal portions of these proteins. In addition, while the SU(VAR)2-10 isoforms are identical up to amino acid 515, they differ at their C-termini. These differences may reflect the ability of different SU(VAR)2-10 isoforms to interact with multiple protein partners, a possibility supported by the variety of binding partners for the different SU(VAR)2-10 orthologs. For example, PIAS 1 and Gu Binding Protein are 98.3% identical, yet were identified in two-hybrid assays using different baits (the Signal Transducer and Activator of Transcription STAT1 and Gu RNA Helicase, respectively (Liu et al. (1998), Proc Natl Acad Sci USA 95, 10626–31; Valdez et al. (1997), Biochem Biophys Res Commun 234, 335–40)). Furthermore, while Miz1 and ARIP3 were identified as two-hybrid binding partners for the homeodomain protein Msx2 and androgen receptor, respectively (Moilanen et al. (1999), J Biol Chem 274, 3700–4; Wu et al. (1997), Mech Dev 65, 3–17), sequence analysis suggests that they are alternative splice variants encoded by the same genetic locus.

TABLE 3

SU(VAR)2-10 Orthologs

| Ortholog | Percent Identity/Similarity, aa121-422 | Function |
|---|---|---|
| human GuBP (Gu Binding Protein) | 57/82 | binds and cleaves Gu, a DEXD boxy RNA Helicase |
| rat KchAP (K+ Channel Associated Protein) | 55/79 | binds and stimulates the membrane association of Kva, a voltage-gated K+ channel subunit |
| mouse Miz1p (Msx-Interacting Zinc finger protein) | 54/79 | Zn finger protein that binds and stimulates DNA binding by Msx2, a homeodomain protein |
| mouse ARIP3 (Androgen Receptor Interacting Protein) | 53/78 | testes-specific modulator of androgen recepto-dependent transcriptional activation |

TABLE 3-continued

SU(VAR)2-10 Orthologs

| Ortholog | Percent Identity/Similarity, aa121-422 | Function |
| --- | --- | --- |
| mouse PIAS3 (Protein Inhibitor of Activated STAT3) | 50/72 | binds and blocks DNA binding by STAT3, a Signal Transducer and Activator of Transcription |

The homology shared between SU(VAR)2–10 and PIAS proteins raises the possibility that one or more SU(VAR) 2–10 isoforms function in the Drosophila JAK-STAT signaling pathway. PIAS proteins appear to function as negative regulators of STAT (Signal Transducer and Activator of Transcription) transcription factors. Other components of the JAK-STAT signaling pathway have been identified in Drosophila, including the Janus kinase hopscotch, (Harrison et al. (1995), Embo J 14, 2857–65), Stat92E (Hou et al. (1996), Cell 84, 411–9; Yan et al. (1996), Cell 84, 421–30), and a putative receptor ligand unpaired (Harrison et al. (1998), Genes Dev 12, 3252–63). Maternal loss of hopscotch and Stat92E and zygotic loss of unpaired result in similar patterning defects in early embryos; however, chromosomal phenotypes have not been examined in these mutants. Mutations that hyperactivate Janus kinase (and presumably STAT) in Drosophila (hopTumorous-lethal) result in lethality, and third instar larvae develop melanotic tumors (Harrison et al. (1995), Embo J 14, 2857–65). It is suggested by the tumor phenotype observed in Su(var)2–10 mutations that a Su(var)2–10 gene product is a bona fide component of the Drosophila JAK-STAT signaling pathway. The role of SU(VAR)2–10 in the JAK-STAT pathway can be addressed with genetic and biochemical interaction analyses.

All of the SU(VAR)2–10 orthologs presented in Table 3 were identified as binding partners for other proteins in yeast two-hybrid assays. The functions of some of the bait proteins used (e.g., the Gu RNA Helicase, and the transcription factors Msx2 and STAT⅓) suggest that the SU(VAR)2–10 orthologs they bind (Gu Binding Protein, Miz1 and PIAS⅓, respectively) are involved in transcriptional regulation. Indeed, the SU(VAR)2–10 ortholog Miz1 possesses DNA binding activity and can act as a transcriptional activator. SU(VAR)2–10 isoforms are likely to act in concert with other proteins, and could function in transcriptional regulation complexes, regulating chromosome structure and function in an indirect manner. However, a role for Su(var)2–10 in transcription does not exclude additional roles in chromosome inheritance. In fact, the two processes can be intimately related. In Saccharomyces cerevisiae, CPF1 acts as a centromere binding protein and a transcriptional regulator (McKenzie et al. (1993), Mol Gen Genet 240, 374–86; Mellor et al. (1990), Embo J 9, 4017–26). In addition, human Centromere Protein C (CENP-C) has been shown to interact with two nucleolar transcription factors, UBF1 and UBF2 (Pluta, A. F., and Earnshaw, W. C. (1996), J Biol Chem 271, 18767–74). These results demonstrate that chromosome inheritance and transcriptional regulation can utilize common factors, and suggest that a common mechanism may link these processes.

SU(VAR)2–10 Protein is Localized in the Nucleoplasm, and is not Found in Mitotic Chromosomes Su(var)2–10 mutations yield multiple chromosomal defects, consistent with a model in which SU(VAR)2–10 proteins localize to chromosomes. Antibodies were raised in Guinea Pig against a 6×His-SU(VAR)2–10 fusion protein containing amino acids 124–354, a region present in the highly conserved central domain of all SU(VAR)2–10 isoforms. The antibodies were affinity purified and analyzed on Western blots, and recognize a doublet at ~60 kD in 0–12 hr cytoplasmic extracts from wild type embryos, consistent with the predicted sizes of the SU(VAR)2–10 isoforms.

The subcellular localization of SU(VAR)2–10 was examined in cell types that display very different types of divisions including the rapid, syncytial nuclear divisions in early embryos, mitotically active diploid larval neuroblasts, and polytenized larval salivary glands. Subcellular localization varies according to the phase of the cell cycle. During interphase, the majority of the protein is cytoplasmic; however, SU(VAR)2–10 protein is also concentrated at the nuclear membrane and in small foci in the nucleoplasm. SU(VAR)2–10 protein displayed a perinuclear pattern in interphase neuroblast cells and distinct foci were present in many nuclei. SU(VAR)2–10 staining was not found in condensed chromosomes during metaphase or anaphase in diploid cells from early embryos or third instar larvae. The absence of SU(VAR)2–10 staining from mitotic chromosomes is not likely to be an artifact of the staining procedure because two different fixation protocols yielded the same results for larval neuroblast tissue. It is intriguing that SU(VAR)2–10 proteins, which are essential for normal chromosome structure and function, do not bind specific sites on mitotic chromosomes. The nuclear membrane localization and foci of staining in embryonic and larval interphase cells suggest that Su(var)2–10 functions during interphase when the nuclear organization of chromosomes is being established (Deinburg et al., (1996), Cell 85, 745–59).

To further investigate SU(VAR)2–10 protein localization, its subcellular distribution in the interphase cells of third instar larval salivary glands was examined. Polytenization allows for better visualization of chromosome and nuclear morphology than in diploid cells. Little if any SU(VAR) 2–10 localized to specific chromosomal regions, consistent with the results from diploid cells. The majority of SU(VAR) 2–10 staining was found in punctate spots that tracked along the edges and on top of chromosomes, and in bridges that appeared to connect chromosome arms. Only a few euchromatic bands appeared to be labeled, including the tip of chromosome 2L. These bands may represent local areas of SU(VAR)2–0 binding, or may be an artifact of the squashed preparation as suggested by protein localization in intact nuclei. Surprisingly, no SU(VAR)2–10 staining was found at the heterochromatic chromocenter in squashed chromosome preparations, despite PEV and inheritance defects which indicate that Su(var)2–10 governs normal heterochromatic functions. This lack of staining could represent the true absence of SU(VAR)2–10 from the chromocenter, or may reflect the underrepresentation of heterochromatin in this tissue (Karpen, G. H., and Spradling, A. C. (1990), Cell 63, 97–107). Nevertheless, the localization of SU(VAR)2–10 to polytene chromosomes appears to be quite distinct from other SU(VAR) and E(VAR) proteins, most notably those involved in transcriptional regulation (e.g., Trl, (Tsukiyama et al. (1994), Nature 367, 525–32)) which bind specific chromosomal bands and are not localized to the nuclear lumen, along the edges of chromosomes, and in the interchromosomal regions.

SU(VAR)2–10 protein localization was examined in unsquashed, intact salivary gland nuclei due to the sheath-like, punctate labeling pattern. In intact nuclei, antibody staining is found near the nuclear membrane, and, consistent with the pattern seen in diploid cells, is absent from the chromosomes. SU(VAR)2–10 staining outlines the chromosomes in whole nuclei in a pattern that defines the edges of chromosome arms when they lie adjacent to the nuclear periphery. A similar scaffold-type localization pattern was seen in whole mount nuclei when an inducible UAS-GFP/SU(VAR)2–10 fusion protein was expressed using an Act5C:Gal4 driver. When expressed in this manner, the fusion protein is unable to fully rescue the lethal phenotype of Su(var)2–10$^1$/Su(var)2–10$^2$ trans-heterozygotes, but does appear to drive animals further in development. Partial rescue could be a function of improper expression, or could be the result of including a single isoform in the GFP/SU(VAR)2–10 construct. Regardless, the similarity in protein distribution seen in the antibody and GFP analyses strongly suggests that the GFP pattern reflects the endogenous protein distribution. Moreover, the unusual localization pattern in intact polytene nuclei indicates that SU(VAR)2–10 may coordinate chromosome-membrane and chromosome-chromosome interactions in interphase cells.

SU(VAR)2–10 and Lamin Colocalize Around the Nuclear Periphery During Interphase To determine whether SU(VAR)2–10 isoforms associated with components of the nuclear membrane during interphase, dual-labeling analyses was performed in neuroblast and salivary gland cells to compare the SU(VAR)2–10 localization pattern to that of nuclear lamin. SU(VAR)2–10 antibodies colocalize with lamin around the nuclear periphery in interphase cells from both cell types. Similar colocalization of these proteins was observed in embryos and in larval fat body. SU(VAR)2–10 is localized to regions in the nuclear lumen in a subset of nuclei, similar to the pattern observed in polytene nuclei. In neuroblast nuclei, the spots of SU(VAR)2–10 localization in the nuclear lumen were distinct and did not colocalize with lamin. In salivary gland nuclei, SU(VAR)2–10 also displayed a distinct localization pattern that is internal to lamin and outlines the nucleolus. These localization data demonstrate that a portion of SU(VAR)2–10 colocalizes with lamin at the nuclear membrane. In addition, SU(VAR)2–10 staining in the nuclear lumen may indicate that different SU(VAR)2–10 isoforms carry out different functions in the interphase nucleus.

Su(var)2–10 belongs to a class of loci that alter heterochromatin-induced gene silencing and are required for chromosome inheritance. These genes may provide the keys to understanding how centromeres are established and maintained. More broadly, data generated from these studies will expand current views on the roles of heterochromatin in regulating chromosome structure and function.

The different phenotypes exhibited by Su(var)2–10 mutants indicate that the protein plays multiple roles in the cell. Defective centromere function is suggested by the decreased transmission of minichromosomes and the defective anaphase movements of endogenous chromosomes. Defects in chromosome condensation are observed during metaphase in diploid cells and in interphase polytene cells. Alterations in gene expression are suggested by the variegation-suppression phenotype, and perhaps the tumor phenotype. Thus, it is possible that SU(VAR)2–10 and the different protein isoforms are required for different cellular processes. However, the different mutant phenotypes are more likely to be caused by defects in a common underlying process, namely aberrant chromosome or chromatin structure.

SU(VAR)2–10 and the Nuclear Organization of Chromosomes

Su(var)2–10 mutants display multiple chromosomal abnormalities in mitotic diploid nuclei and interphase salivary gland nuclei, as well as affects on gene expression. SU(VAR)2–10 proteins colocalize with lamin around the nuclear periphery during interphase in diverse tissues, and surrounds or sheaths chromosomes in polytene nuclei. Given multiple inheritance and expression phenotypes, it is surprising that the SU(VAR)2–10 protein does not appear to be in interphase polytene chromosomes or mitotic diploid chromosomes.

The organization of chromosomes in the interphase nucleus is a coordinated, nonrandom process; however, defining the causes and consequences of nuclear organization remains a nascent field of study (reviewed in Bridger and Bickmore (1998). Trends Genet 14, 403–9). Current data indicate that interphase chromosomes can exhibit at least three general levels of nuclear architecture, which are generally consistent across diverse cell types (e.g., diploid vs. polytene cells.) First, chromosomes can be organized in a Rabl configuration with centromeres at one end of the nucleus and telomeres at the other (Dernburg et al., (1996), Cell 85, 745–59). Second, chromosomes are not intertwined within the nucleus; rather, they occupy distinct domains (Hochstrasser et al. (1986), J Cell Biol 102, 112–23). Third, a discrete set of loci are in close contact with the nuclear envelope (Marshall et al. (1996), Mol Biol Cell 7, 825–42). The nonrandom organization of interphase chromosomes is intriguing given the various chromosomal functions associated with the nuclear membrane. The perinuclear localization of genes in *S. cerevisiae* can induce transcriptional silencing (Andrulis et al. (1998), Nature 394, 592–5), and in Drosophila embryos focal points for chromosome condensation occur near the nuclear periphery in interphase nuclei (Hiraoka et al. (1989), Nature 342, 293–6). Furthermore, interphase centromeres in mammalian cells tend to cluster at the nuclear periphery and around nucleoli (reviewed in (Pluta et al. (1995), Science 270, 1591–4)). Nuclear organization defects in interphase could result in multiple chromosomal abnormalities, including altered gene expression, defective chromosome condensation at prophase and aberrant centromere function in metaphase and anaphase, all phenotypes exhibited by Su(var)2–10 mutants. Su(var)2–10 participates in organizing chromosomes in the interphase nucleus, and helps generate the precise chromatin structure required for gene expression, chromosome condensation, centromere function and subsequent mitotic chromosome segregation events.

Su(var)2–10 and Centromere Function

Genetic interaction data and visible anaphase defects suggest that Su(var)2–10 gene products affect centromere function, which could be accomplished in two different ways. First, SU(VAR)2–10 protein may interact directly with the centromere. If so, there must be a small amount of protein at centromeres during mitosis, or the protein may be transiently associated with centromeres during specific stage (s) in the cell cycle, because we do not detect the protein at centromeres in mitotic larval neuroblasts or embryos. Localization to centromeres during interphase cannot be addressed at this time, because the 'span-nuclear' distribution of the protein may mask centromere localization. Furthermore, individual chromosomes are not cytologically visible during interphase, and the centromere-specific probes necessary to identify the locations of Drosophila centromeres in interphase nuclei are not available. Dynamic, cell cycle stage-specific localization is seen for PROD (Proliferation Disrupter), a putative centromere-binding protein in Drosophila (Platero et al. (1998), J Cell Biol 140, 1297–306; Torok et al. (1997), Genes Dev 11, 213–25).

Second, SU(VAR)2–10 may affect centromere function indirectly, for example by acting at the nuclear membrane during interphase to prepare chromosomes for successful centromere activity at the following metaphase and anaphase. Su(var)2–10 mutants displayed defects in chromatin condensation in all chromosomal regions. A general defect in chromatin condensation could affect kinetochore assembly, sister chromatid cohesion or sister chromatid separation. While the altered dosage of Su(var)2–10 had no affect on the function of full sized centromeres in the minichromosome assay, the function of partially deleted centromeres was reduced. These observations combined with the dominant PEV suppression phenotype suggest that heterochromatin assembly is exquisitely sensitive to cellular Su(var)2–10 levels. General condensation defects could explain at least part of the centromere defects observed in Su(var)2–10 mutants, but it is also possible that one or more SU(VAR)2–10 isoforms are dedicated to centromere-specific functions. An intriguing possibility is that Su(var)2–10 is involved in the epigenetic marking of centromeres, and improper marking in mutants could produce centromere defects.

A Model for SU(VAR)2–10 Function

Figure 3:
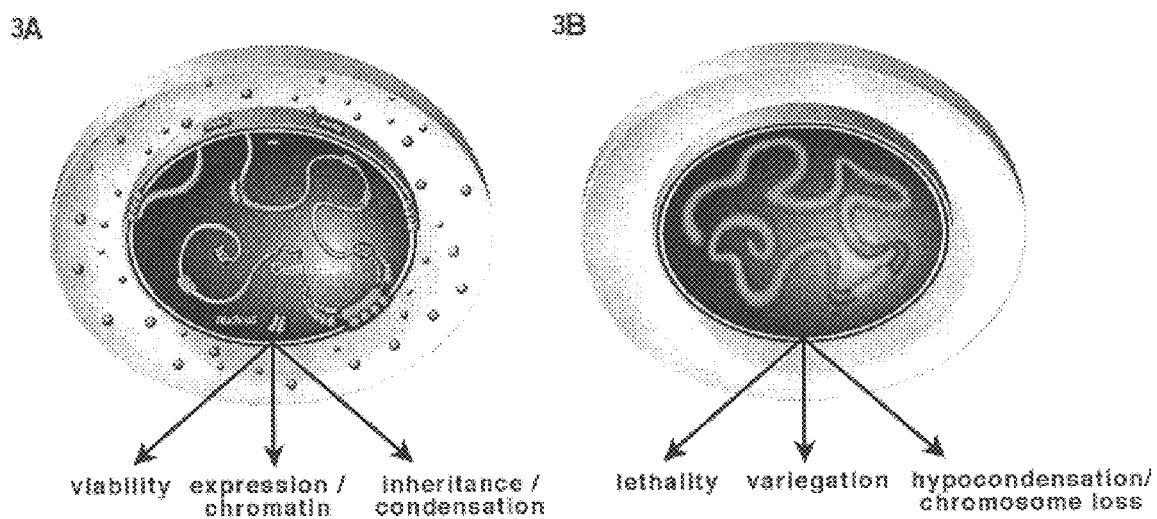
FIGS. 3A–3B show a model for Su(var)2–10 function. Su(var)2–10 locus promotes normal chromosome structure and nuclear organization. In a wild type cell (A) SU(VAR)2–10 protein is present in the cytoplasm and the nucleus, where the predominant localization observed is at the nuclear membrane (colocalized with lamin) and along chromosome arms. SU(VAR)2–10 protein links specific chromosome regions to the nuclear periphery and mediates interactions between chromosome regions, and that these functions are necessary to the normal three-dimensional organization of chromosomes in the nucleus, chromosome condensation, heterochromatin structure and centromere function (thick tubes). The chromosome sheath may play an independent role in chromosome structure and function, for example in regulating local chromatin structure or protein concentrations. (B) In the absence of SU(VAR)2–10 protein chromosomes lose their association with the nuclear membrane and other chromosomal regions, become disorganized and hypocondensed, leading to the lethal, variegation suppression, and chromosome inheritance phenotypes.

The diverse Su(var)2–10 mutant phenotypes suggest that SU(VAR)2–10 or distinct SU(VAR)2–10 isoforms regulate different cellular functions. SU(VAR)2–10 protein links heterochromatin and other chromosomal regions to the nuclear membrane, and thus affect the organization of chromosomes within the nucleus (FIG. 3A). In addition, nucleoplasmic SU(VAR)2–10, which appears to ensheath chromosomes, may be part of a structure that regulates chromatin structure or facilitates protein-protein or protein-DNA interactions by concentrating factors at the chromosome surface. Su(var)2–10 contributes to viability, gene expression and chromosome inheritance by establishing preconditions for successful heterochromatin formation, centromere structure and global chromosome condensation (which is known to initiate at the nuclear periphery, Hiraoka et al. (1989), Nature 342, 293–6). The absence of SU(VAR)2–10 protein in mutant animals (FIG. 3B) could lead to aberrant associations between chromosomes and the nuclear periphery, mislocalization of chromosomes within the nucleus, and altered chromatin structure, resulting in the observed hypocondensation, chromosome loss and lethality phenotypes. The dominant Su(var) phenotype is characterized by improved expression of genes that are abnormally placed near heterochromatin (e.g. white, FIG. 2), and can also be explained by a role for SU(VAR)2–10 in global chromosome condensation, chromatin structure or nuclear organization. The expression of genes juxtaposed with heterochromatin could be improved in Su(var)2–10/+ animals because of general chromatin decondensation or unwinding, or because the organization of chromosomes within the nucleus is altered in a way that increases the probability that the affected gene will be positioned within a nuclear compartment or domain that allows transcription (Wakimoto, B. T. (1998), Cell 93, 321–4).

Genetic analysis. All genetic crosses were carried out at 25° C., and minichromsome transmission assays were performed as described previously (Cook et al. (1997), Genetics 145, 737–47). The two Su(var)2–10 EMS alleles used in this study were kindly provided by Gunter Reuter (Wustmann et al. (1989), Mol Gen Genet 217, 520–7). Stocks used in deficiency mapping Su(var)2–10 were obtained from the Bloomington and Umea Drosophila Stock Centers. The Su(var)2–10$^{03697}$ allele (originally denoted P{PZ}1(2) 03697$^{03697}$) (Spradling et al. (1999), Genetics 153, 135–77) and GFP Balancer chromosomes (Casso et al. (1999), Mech Dev 88, 229–232) were provided by the Bloomington Drosophila Stock Center. Precise and imprecise excisions of the Su(var)2–10$^1$(2)$^{03697}$ P element were generated by genetically introducing a source of transposase to fly lines bearing the P element (Robertson et al. (1988), Genetics 118, 461–70). Mobilization events were selected based on loss of the rosy+eye color marker, and single events were established into stocks for further analyses. In all analyses presented, "wild type" refers to our standard yl; ry506 fly line, and +/+ indicates the status of the Su(var)2–10 locus in this stock.

Mitotic defects. Mitotic chromosome squashes were generated to look for defects in endogenous chromosome behavior (X and/or Y, second, third, and fourth chromosomes). Mitotic figures were prepared from third-instar larval brain tissue as described in "protocol 2" of (Gatti et al. (1994), Methods Cell Biol. 44, 371–391) except neither hypotonic incubation nor colchicine treatment was used. Su(var)2–10$^1$/Su(var)2–10$^2$ trans-heterozygous larvae were analyzed to eliminate the impact of additional mutations present along these chromosomes. Mitotic figures from mutants were compared to those from wild type control larvae. At least fifty fields per brain were scored for metaphase and anaphase figures, where a field was defined as the region visible at 100×magnification with 1.25×optivar on a Zeiss Axiophot fluorescence microscope. Metaphase figures were classified as hypocondensed when individual sister chromatids of the major autosomes could not be distinguished. The rare appearance of aneuploid metaphase figures in mutant brains were not included in quantitating the mitotic defects. The mitotic index (M.I.) was calculated as the total number of metaphase plus anaphase figures divided by the total number of fields scored cDNA library screening and EST mapping. Plasmid rescue of genomic DNA flanking the Su(var)2–10$^{03697}$ insertion yielded two fragments: a 5 kb XhoI and a 0.9 kb XhoI-NheI fragment. Both fragments were used to probe an embryonic cDNA library, and six Su(var)2–10 cDNAs were isolated. Subsequent analyses of the Berkeley Drosophila Genome Project (BDGP) database identified numerous expressed sequence tags (ESTs) which were used to generate a more complete set of Su(var)2–10 cDNAs.

Transgene construction and transformation rescue experiments. The 5 kb XhoI-XhoI plasmid rescue fragment was used to screen a collection of BDGP P1 clones from polytene region 45A using standard Southern blot analyses. P12099 and P1300 hybridized strongly with this probe, and comparing the restriction map of P1300 to the Su(var)2–10 sequence indicated that the locus was fully contained within a 15 kb EcoRI fragment. This genomic DNA fragment was isolated and subcloned into the pYES germ line transformation rescue vector (Patton et al., 1992). Embryo injections for germ line transformation were performed using our standard yl; ry$^{506}$ background, and transformants were selected based on the expression of the y+body color marker. A transformant was isolated in which the 15 kb EcoRI fragment was inserted on the X chromosome. A stable stock was generated, and this line was used in lethality and minichromosome transmission rescue experiments. The element was remobilized to generate third chromosome inserts for rescue of the PEV suppression phenotype.

Analyzing the Su(var)2–10 alleles. To sequence the Su(var)2–10$^1$ and Su(var)2–10$^2$ alleles, single embryo PCR was performed using primers that span the SU(VAR)2–10 coding region. Each Su(var)2–10 allele was outcrossed to the wild type Oregon R strain and eggs from crosses of Su(var)2–10 heterozygous siblings were collected onto apple juice-agar plates and allowed to develop. After 24 hours, unhatched, individual embryos were collected, and prepped for single embryo PCR. DNA from at least two embryos for each genotype was used for each primer set. PCR products were analyzed for purity on agarose gels, purified using the Qiaquick PCR Purification kit (Qiagen, Valencia, Calif.) and DNA sequences were determined using an ABI377 automated sequencer (Perkin Elmer, Foster City, Calif.). The sequences were aligned and analyzed using the Sequencher software package (Gene Codes Corp., Ann Arbor, Mich.). As parental chromosomes were unavailable for this analysis, sequence changes were determined by comparing the sequences of the Su(var)2–101 allele to the Su(var)2–102 allele, and by comparing both to yl; ry506 controls. No other sequence differences beyond those described were found between the ORFs for Su(var)2–10$^1$ and Su(var)2–10$^2$.

Su(var)2–1003697 excisions were defined as precise or imprecise based on complementation, Southern blot and PCR analyses. Of 117 excisions subject to these analyses, 31 were precise and 86 imprecise. Twelve imprecise excisions that deleted sequences 5' of the P element insertion site complemented Su(var)2–10$^1$ for lethality. Four imprecise excisions, including Su(var)2–10$^{Pex74a}$ (FIG. 2B), failed to complement Su(var)2–10$^1$ for lethality and deleted 3' into the coding region. Su(var)2–10$^{Pex74a}$ removes all of the Su(var)2–10 coding sequences.

Northern analysis. Total RNA was isolated from the indicated developmental stages using the Purescript RNA Isolation Kit (Gentra Systems, Inc., Minneapolis, Minn.) Messenger RNA was isolated using the Oligotex mRNA Isolation Kit (Qiagen, Valencia, Calif.), and 1.5 $\mu$g–2.5 $\mu$g of poly-A+RNA was loaded per lane. Formaldehyde gels were run overnight and blotted to Hybond-N+nylon membranes using standard techniques. Blots were probed with Su(var)2–10 cDNAs, then stripped and reprobed with Rp49 probes as a loading control.

Generating SU(VAR)2–10 antibodies. PCR was used to generate a 690 bp fragment (representing amino acids 124–354) from the middle portion of Su(var)2–10. Primers were designed to append a 5' BamHI and a 3' SalI site to the ends of the PCR fragment. The PCR product was digested with these enzymes and cloned into a 6×His-tagging vector (pQE-30, Qiagen, Valencia, Calif.). The tag was added to the N-terminus of this 230aa fragment. The fusion protein was expressed in *Escherichia coli* and purified over a Ni-NTA column. Three extra bands co-eluted from the Ni-NTA column with the fusion protein and fractions containing the fusion protein were pooled and further purified over Mono-Q and Mono-S columns. All four bands co-eluted from both columns. Western blotting with anti-RGS-HIS antibodies (Qiagen, Valencia, Calif.) that recognize the 6×His tag recognized all four bands, indicating that these were degradation products of the 6×His/SU(VAR)2–10 fusion protein. Preparative gels were run and the full-length fusion protein was excised from these gels for use in raising Guinea Pig antibodies (Covance, Berkeley, Calif.).

Western analysis. SU(VAR)2–10 antibodies were affinity purified from Western blots using the 6×His/ SU(VAR)2–10 fusion protein. 10 $\mu$l of purified cytoplasmic extract from 0–12 hr embryos (a gift from Jim Kadonaga) was electrophoresed through a 12.5% SDS-PAGE gel. The gel was transferred onto PVDF membrane using a Bio-Rad (Hercules, Calif.) electrophoretic transfer cell. The blot was probed with a 1:100 dilution of affinity purified anti-SU (VAR)2–10 antibody, and a 1:5000 dilution of a horseradish peroxidase-conjugated Goat anti-Guinea Pig secondary antibody (Chemicon, Temecula, Calif.). Bands were visualized using ECL Western blotting detection reagents (Amersham Pharmacia Biotech, Piscataway, N.J.).

Antibody staining. Antibody staining of embryos and squashed polytene chromosomes was carried out using methods outlined in Theurkauf, W. E. (1994), Methods Cell Biol. 44, 489–505; and Andrew, D. J., and Scott, M. P. (1994), Methods Cell Biol. 44, 353–70, respectively. Whole mount salivary gland staining was performed as described in Goldberg et al. (1998), Mol Cell Biol 18, 4315–23). Two protocols were used to prepare and stain squashed neuroblast tissue. Protocol 1 was the same protocol used for squashed polytene chromosome staining (Andrew, D. J., and Scott, M. P. (1994), Methods Cell Biol. 44, 353–70). Protocol 2 is described in (Fanti et al. (1998), Mol Cell 2, 527–38). Protocol 1 uses a formaldehyde:acetic acid fixative that includes Tween-20 and polyamines, while protocol 2 uses methanol:acetic acid fixation. In all cases, affinity-purified Guinea Pig anti-SU(VAR)2–10 primary antibodies were diluted 1:5; monoclonal anti-lamin primaries (T47, generated by D. Glover, provided by the Wasserman lab) were used at 1:10; Goat anti-Guinea Pig-FITC and Goat anti-Mouse-Cy3 secondaries (Chemicon, Temecula, Calif.) were used at 1:100. Protein localization patterns for all figures except 6D–F were analyzed using a Zeiss Axiophot fluorescence microscope equipped with a cooled CCD camera. Images were captured and pseudocolored using EP Lab Spectrum Imaging Software (Scanalytics, Inc., Vienna, Va.) and merged using Adobe Photoshop.

While the invention has been described in detail with reference to certain preferred embodiments thereof, it will be understood that modifications and variations are within the spirit and scope of that which is described and claimed.

What is claimed is:

1. A polypeptide comprising a sequence as set forth in SEQ ID NO:2 and conservative variants thereof.

2. A polypeptide comprising a sequence as set forth in SEQ ID NO:4 and conservative variants thereof.

* * * * *

SEQUENCE LISTING

<160> NUMBER OF SEQ ID NOS: 5

<210> SEQ ID NO 1
<211> LENGTH: 1611
<212> TYPE: DNA
<213> ORGANISM: Drosophila melanogaster
<220> FEATURE:
<221> NAME/KEY: CDS
<222> LOCATION: (1)..(1611)

<400> SEQUENCE: 1

| | | | | | | | | | | | | | | | | |
|---|---|---|---|---|---|---|---|---|---|---|---|---|---|---|---|---|
| atg | gtg | cag | atg | ctt | cga | gtg | gtc | gag | ctg | caa | aaa | atc | ctg | tcg | ttt | 48 |
| Met | Val | Gln | Met | Leu | Arg | Val | Val | Glu | Leu | Gln | Lys | Ile | Leu | Ser | Phe | |
| 1 | | | | 5 | | | | | 10 | | | | | 15 | | |
| ctg | aac | atc | tca | ttc | gct | gga | cga | aaa | act | gac | ctg | cag | agc | cgc | atc | 96 |
| Leu | Asn | Ile | Ser | Phe | Ala | Gly | Arg | Lys | Thr | Asp | Leu | Gln | Ser | Arg | Ile | |
| | | | 20 | | | | | 25 | | | | | 30 | | | |
| ctc | tcg | ttc | ttg | cgc | acc | aac | ttg | gaa | ctg | ctt | gcc | ccg | aag | gtc | cag | 144 |
| Leu | Ser | Phe | Leu | Arg | Thr | Asn | Leu | Glu | Leu | Leu | Ala | Pro | Lys | Val | Gln | |
| | | 35 | | | | | 40 | | | | | 45 | | | | |
| gaa | gtc | tac | gcc | cag | tcc | gtg | cag | gaa | caa | aac | gcc | acg | ctg | cag | tac | 192 |
| Glu | Val | Tyr | Ala | Gln | Ser | Val | Gln | Glu | Gln | Asn | Ala | Thr | Leu | Gln | Tyr | |
| | 50 | | | | | 55 | | | | | 60 | | | | | |
| atc | gac | cca | acc | agg | atg | tac | tcg | cac | atc | cag | ctg | ccg | ccc | acc | gtg | 240 |
| Ile | Asp | Pro | Thr | Arg | Met | Tyr | Ser | His | Ile | Gln | Leu | Pro | Pro | Thr | Val | |
| 65 | | | | | 70 | | | | | 75 | | | | | 80 | |
| cag | ccc | aat | ccc | gtg | ggc | ctc | gtg | ggc | agc | ggc | caa | ggt | gtg | caa | gtg | 288 |
| Gln | Pro | Asn | Pro | Val | Gly | Leu | Val | Gly | Ser | Gly | Gln | Gly | Val | Gln | Val | |
| | | | | 85 | | | | | 90 | | | | | 95 | | |
| ccc | ggc | ggc | cag | atg | aat | gtg | gtc | ggc | ggc | gca | ccc | ttc | ctc | cac | aca | 336 |
| Pro | Gly | Gly | Gln | Met | Asn | Val | Val | Gly | Gly | Ala | Pro | Phe | Leu | His | Thr | |
| | | | 100 | | | | | 105 | | | | | 110 | | | |
| cac | agc | atc | aac | agc | cag | ctg | cct | att | cac | ccc | gat | gtg | cgg | ctg | aaa | 384 |
| His | Ser | Ile | Asn | Ser | Gln | Leu | Pro | Ile | His | Pro | Asp | Val | Arg | Leu | Lys | |
| | | | 115 | | | | | 120 | | | | | 125 | | | |
| aag | cta | gcc | ttc | tac | gat | gta | ctc | gga | acg | cta | att | aag | cct | tca | act | 432 |
| Lys | Leu | Ala | Phe | Tyr | Asp | Val | Leu | Gly | Thr | Leu | Ile | Lys | Pro | Ser | Thr | |
| | 130 | | | | | 135 | | | | | 140 | | | | | |
| ctg | gtg | cca | cgc | aac | act | cag | cgc | gtc | caa | gag | gtg | cct | ttc | tac | ttc | 480 |
| Leu | Val | Pro | Arg | Asn | Thr | Gln | Arg | Val | Gln | Glu | Val | Pro | Phe | Tyr | Phe | |
| 145 | | | | | 150 | | | | | 155 | | | | | 160 | |
| acg | ctc | acg | ccg | cag | cag | gcc | acc | gag | att | gcc | tcc | aat | cgc | gac | att | 528 |
| Thr | Leu | Thr | Pro | Gln | Gln | Ala | Thr | Glu | Ile | Ala | Ser | Asn | Arg | Asp | Ile | |
| | | | | 165 | | | | | 170 | | | | | 175 | | |
| cgc | aac | agc | tcc | aag | gtg | gag | cac | gcc | att | cag | gtt | caa | ctg | cgc | ttt | 576 |
| Arg | Asn | Ser | Ser | Lys | Val | Glu | His | Ala | Ile | Gln | Val | Gln | Leu | Arg | Phe | |
| | | | 180 | | | | | 185 | | | | | 190 | | | |
| tgc | ctg | gtg | gag | act | tcg | tgc | gac | cag | gag | gac | tgc | ttc | ccg | ccg | aac | 624 |
| Cys | Leu | Val | Glu | Thr | Ser | Cys | Asp | Gln | Glu | Asp | Cys | Phe | Pro | Pro | Asn | |
| | | | 195 | | | | | 200 | | | | | 205 | | | |
| gta | aac | gtc | aaa | gtg | aac | aac | aaa | ctc | tgt | cag | ctg | cct | aat | gtc | att | 672 |
| Val | Asn | Val | Lys | Val | Asn | Asn | Lys | Leu | Cys | Gln | Leu | Pro | Asn | Val | Ile | |
| | | 210 | | | | | 215 | | | | | 220 | | | | |
| cct | aca | aac | cga | cca | aat | gtg | gag | ccc | aac | gct | ccg | ccg | cga | ccc | gtt | 720 |
| Pro | Thr | Asn | Arg | Pro | Asn | Val | Glu | Pro | Asn | Ala | Pro | Pro | Arg | Pro | Val | |
| 225 | | | | | 230 | | | | | 235 | | | | | 240 | |
| aat | gtc | acg | tcc | aat | gta | aag | ctg | tcg | cct | acc | gtc | acc | aac | acc | ata | 768 |
| Asn | Val | Thr | Ser | Asn | Val | Lys | Leu | Ser | Pro | Thr | Val | Thr | Asn | Thr | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| acg | gtt | cag | tgg | tgt | ccg | gac | tac | act | cgt | agc | tac | tgt | ctg | gcc | gta | 816 |
| Thr | Val | Gln | Trp | Cys | Pro | Asp | Tyr | Thr | Arg | Ser | Tyr | Cys | Leu | Ala | Val | |
| | | | 260 | | | | 265 | | | | | 270 | | | | |
| tac | ctg | gta | aag | aag | ctc | acc | tca | aca | cag | ctt | ttg | cag | cga | atg | aag | 864 |
| Tyr | Leu | Val | Lys | Lys | Leu | Thr | Ser | Thr | Gln | Leu | Leu | Gln | Arg | Met | Lys | |
| | | | 275 | | | | | 280 | | | | | 285 | | | |
| acg | aag | ggc | gta | aaa | cca | gcg | gac | tac | acg | cga | ggc | tta | atc | aaa | gag | 912 |
| Thr | Lys | Gly | Val | Lys | Pro | Ala | Asp | Tyr | Thr | Arg | Gly | Leu | Ile | Lys | Glu | |
| | | 290 | | | | | 295 | | | | | 300 | | | | |
| aag | ctg | act | gag | gat | gct | gac | tgc | gaa | ata | gcc | acc | act | atg | ctg | aag | 960 |
| Lys | Leu | Thr | Glu | Asp | Ala | Asp | Cys | Glu | Ile | Ala | Thr | Thr | Met | Leu | Lys | |
| 305 | | | | | 310 | | | | | 315 | | | | | 320 | |
| gtt | tcc | ctt | aac | tgc | ccg | atg | ggc | aag | atg | aaa | atg | ttg | ctg | cct | tgt | 1008 |
| Val | Ser | Leu | Asn | Cys | Pro | Met | Gly | Lys | Met | Lys | Met | Leu | Leu | Pro | Cys | |
| | | | | 325 | | | | | 330 | | | | | 335 | | |
| cga | gca | tca | acc | tgc | tcg | cat | ctg | caa | tgc | ttc | gat | gcc | agt | ctc | tac | 1056 |
| Arg | Ala | Ser | Thr | Cys | Ser | His | Leu | Gln | Cys | Phe | Asp | Ala | Ser | Leu | Tyr | |
| | | | 340 | | | | | 345 | | | | | 350 | | | |
| ctg | caa | atg | aat | gag | cgt | aag | ccc | acg | tgg | aac | tgc | cct | gta | tgc | gac | 1104 |
| Leu | Gln | Met | Asn | Glu | Arg | Lys | Pro | Thr | Trp | Asn | Cys | Pro | Val | Cys | Asp | |
| | | | 355 | | | | | 360 | | | | | 365 | | | |
| aag | ccg | gcc | att | tat | gac | aac | ctg | gtc | ata | gat | ggc | tac | ttc | cag | gag | 1152 |
| Lys | Pro | Ala | Ile | Tyr | Asp | Asn | Leu | Val | Ile | Asp | Gly | Tyr | Phe | Gln | Glu | |
| | 370 | | | | | 375 | | | | | 380 | | | | | |
| gtg | ttg | ggc | tcg | tcg | ctt | cta | aag | agt | gat | gat | act | gag | att | caa | ctt | 1200 |
| Val | Leu | Gly | Ser | Ser | Leu | Leu | Lys | Ser | Asp | Asp | Thr | Glu | Ile | Gln | Leu | |
| 385 | | | | | 390 | | | | | 395 | | | | | 400 | |
| cat | cag | gat | gga | tct | tgg | agc | aca | cca | gga | tta | cgg | agc | gag | acg | cag | 1248 |
| His | Gln | Asp | Gly | Ser | Trp | Ser | Thr | Pro | Gly | Leu | Arg | Ser | Glu | Thr | Gln | |
| | | | | 405 | | | | | 410 | | | | | 415 | | |
| atc | ctt | gat | acg | cct | tca | aag | ccc | gcc | caa | aag | gtt | gag | gtt | ata | tcg | 1296 |
| Ile | Leu | Asp | Thr | Pro | Ser | Lys | Pro | Ala | Gln | Lys | Val | Glu | Val | Ile | Ser | |
| | | | 420 | | | | | 425 | | | | | 430 | | | |
| gat | gac | ata | gaa | ctt | atc | tcg | gat | gac | gcc | aag | cca | gta | aag | agg | gat | 1344 |
| Asp | Asp | Ile | Glu | Leu | Ile | Ser | Asp | Asp | Ala | Lys | Pro | Val | Lys | Arg | Asp | |
| | | | 435 | | | | | 440 | | | | | 445 | | | |
| ttg | tcc | cca | gca | cag | gac | gaa | cag | ccc | aca | tca | acg | tca | aac | agt | gaa | 1392 |
| Leu | Ser | Pro | Ala | Gln | Asp | Glu | Gln | Pro | Thr | Ser | Thr | Ser | Asn | Ser | Glu | |
| | 450 | | | | | 455 | | | | | 460 | | | | | |
| act | gtt | gac | cta | acg | tta | agc | gat | tca | gac | gac | gac | atg | ccg | ctg | gct | 1440 |
| Thr | Val | Asp | Leu | Thr | Leu | Ser | Asp | Ser | Asp | Asp | Asp | Met | Pro | Leu | Ala | |
| 465 | | | | | 470 | | | | | 475 | | | | | 480 | |
| aag | cgt | tgt | ccg | ccc | gcc | aag | caa | gcc | gtc | gcc | agt | tcc | acg | tcg | aac | 1488 |
| Lys | Arg | Cys | Pro | Pro | Ala | Lys | Gln | Ala | Val | Ala | Ser | Ser | Thr | Ser | Asn | |
| | | | | 485 | | | | | 490 | | | | | 495 | | |
| ggc | agc | ggt | ggc | ggc | caa | cgt | gcc | tat | acc | ccg | gca | cag | cag | ccc | cag | 1536 |
| Gly | Ser | Gly | Gly | Gly | Gln | Arg | Ala | Tyr | Thr | Pro | Ala | Gln | Gln | Pro | Gln | |
| | | | 500 | | | | | 505 | | | | | 510 | | | |
| caa | tcc | gag | gat | aat | gac | gaa | aac | tgt | acg | gct | aag | gcc | aaa | gag | gat | 1584 |
| Gln | Ser | Glu | Asp | Asn | Asp | Glu | Asn | Cys | Thr | Ala | Lys | Ala | Lys | Glu | Asp | |
| | | | 515 | | | | | 520 | | | | | 525 | | | |
| tcc | gta | att | gat | ttt | cta | gat | tcg | cca | | | | | | | | 1611 |
| Ser | Val | Ile | Asp | Phe | Leu | Asp | Ser | Pro | | | | | | | | |
| | | | 530 | | | | | 535 | | | | | | | | |

<210> SEQ ID NO 2
<211> LENGTH: 537
<212> TYPE: PRT
<213> ORGANISM: Drosophila melanogaster

<400> SEQUENCE: 2

```
Met Val Gln Met Leu Arg Val Glu Leu Gln Lys Ile Leu Ser Phe
 1               5                  10                  15

Leu Asn Ile Ser Phe Ala Gly Arg Lys Thr Asp Leu Gln Ser Arg Ile
            20                  25                  30

Leu Ser Phe Leu Arg Thr Asn Leu Glu Leu Leu Ala Pro Lys Val Gln
        35                  40                  45

Glu Val Tyr Ala Gln Ser Val Gln Glu Gln Asn Ala Thr Leu Gln Tyr
    50                  55                  60

Ile Asp Pro Thr Arg Met Tyr Ser His Ile Gln Leu Pro Pro Thr Val
65                  70                  75                  80

Gln Pro Asn Pro Val Gly Leu Val Gly Ser Gly Gln Gly Val Gln Val
                85                  90                  95

Pro Gly Gly Gln Met Asn Val Val Gly Gly Ala Pro Phe Leu His Thr
                100                 105                 110

His Ser Ile Asn Ser Gln Leu Pro Ile His Pro Asp Val Arg Leu Lys
            115                 120                 125

Lys Leu Ala Phe Tyr Asp Val Leu Gly Thr Leu Ile Lys Pro Ser Thr
        130                 135                 140

Leu Val Pro Arg Asn Thr Gln Arg Val Gln Glu Val Pro Phe Tyr Phe
145                 150                 155                 160

Thr Leu Thr Pro Gln Gln Ala Thr Glu Ile Ala Ser Asn Arg Asp Ile
                165                 170                 175

Arg Asn Ser Ser Lys Val Glu His Ala Ile Gln Val Gln Leu Arg Phe
                180                 185                 190

Cys Leu Val Glu Thr Ser Cys Asp Gln Glu Asp Cys Phe Pro Pro Asn
            195                 200                 205

Val Asn Val Lys Val Asn Asn Lys Leu Cys Gln Leu Pro Asn Val Ile
            210                 215                 220

Pro Thr Asn Arg Pro Asn Val Glu Pro Asn Ala Pro Pro Arg Pro Val
225                 230                 235                 240

Asn Val Thr Ser Asn Val Lys Leu Ser Pro Thr Val Thr Asn Thr Ile
                245                 250                 255

Thr Val Gln Trp Cys Pro Asp Tyr Thr Arg Ser Tyr Cys Leu Ala Val
                260                 265                 270

Tyr Leu Val Lys Lys Leu Thr Ser Thr Gln Leu Leu Gln Arg Met Lys
        275                 280                 285

Thr Lys Gly Val Lys Pro Ala Asp Tyr Thr Arg Gly Leu Ile Lys Glu
        290                 295                 300

Lys Leu Thr Glu Asp Ala Asp Cys Glu Ile Ala Thr Thr Met Leu Lys
305                 310                 315                 320

Val Ser Leu Asn Cys Pro Met Gly Lys Met Lys Met Leu Leu Pro Cys
                325                 330                 335

Arg Ala Ser Thr Cys Ser His Leu Gln Cys Phe Asp Ala Ser Leu Tyr
            340                 345                 350

Leu Gln Met Asn Glu Arg Lys Pro Thr Trp Asn Cys Pro Val Cys Asp
            355                 360                 365

Lys Pro Ala Ile Tyr Asp Asn Leu Val Ile Asp Gly Tyr Phe Gln Glu
    370                 375                 380

Val Leu Gly Ser Ser Leu Leu Lys Ser Asp Asp Thr Glu Ile Gln Leu
385                 390                 395                 400

His Gln Asp Gly Ser Trp Ser Thr Pro Gly Leu Arg Ser Glu Thr Gln
                405                 410                 415
```

-continued

```
Ile Leu Asp Thr Pro Ser Lys Pro Ala Gln Lys Val Glu Val Ile Ser
        420                 425                 430

Asp Asp Ile Glu Leu Ile Ser Asp Ala Lys Pro Val Lys Arg Asp
        435                 440                 445

Leu Ser Pro Ala Gln Asp Glu Gln Pro Thr Ser Thr Ser Asn Ser Glu
    450                 455                 460

Thr Val Asp Leu Thr Leu Ser Asp Ser Asp Asp Met Pro Leu Ala
465                 470                 475                 480

Lys Arg Cys Pro Pro Ala Lys Gln Ala Val Ala Ser Ser Thr Ser Asn
                    485                 490                 495

Gly Ser Gly Gly Gln Arg Ala Tyr Thr Pro Ala Gln Gln Pro Gln
            500                 505                 510

Gln Ser Glu Asp Asn Asp Glu Asn Cys Thr Ala Lys Ala Lys Glu Asp
        515                 520                 525

Ser Val Ile Asp Phe Leu Asp Ser Pro
        530                 535
```

<210> SEQ ID NO 3
<211> LENGTH: 1611
<212> TYPE: DNA
<213> ORGANISM: Drosophila melanogaster
<220> FEATURE:
<221> NAME/KEY: CDS
<222> LOCATION: (1)..(1611)

<400> SEQUENCE: 3

```
atg gtg cag atg ctt cga gtg gtc gag ctg caa aaa atc ctg tcg ttt      48
Met Val Gln Met Leu Arg Val Val Glu Leu Gln Lys Ile Leu Ser Phe
  1               5                  10                  15 ctg aac atc tca ttc gct gga cga aaa act gac ctg cag agc cgc atc      96
Leu Asn Ile Ser Phe Ala Gly Arg Lys Thr Asp Leu Gln Ser Arg Ile
             20                  25                  30 ctc tcg ttc ttg cgc acc aac ttg gaa ctg ctt gcc ccg aag gtc cag     144
Leu Ser Phe Leu Arg Thr Asn Leu Glu Leu Leu Ala Pro Lys Val Gln
         35                  40                  45 gaa gtc tac gcc cag tcc gtg cag gaa caa aac gcc acg ctg cag tac     192
Glu Val Tyr Ala Gln Ser Val Gln Glu Gln Asn Ala Thr Leu Gln Tyr
     50                  55                  60 atc gac cca acc agg atg tac tcg cac atc cag ctg ccg ccc acc gtg     240
Ile Asp Pro Thr Arg Met Tyr Ser His Ile Gln Leu Pro Pro Thr Val
 65                  70                  75                  80 cag ccc aat ccc gtg ggc ctc gtg ggc agc ggc caa ggt gtg caa gtg     288
Gln Pro Asn Pro Val Gly Leu Val Gly Ser Gly Gln Gly Val Gln Val
                 85                  90                  95 ccc ggc ggc cag atg aat gtg gtc ggc ggc gca ccc ttc ctc cac aca     336
Pro Gly Gly Gln Met Asn Val Val Gly Gly Ala Pro Phe Leu His Thr
            100                 105                 110 cac agc atc aac agc cag ctg cct att cac ccc gat gtg cgg ctg aaa     384
His Ser Ile Asn Ser Gln Leu Pro Ile His Pro Asp Val Arg Leu Lys
        115                 120                 125 aag cta gcc ttc tac gat gta ctc gga acg cta att aag cct tca act     432
Lys Leu Ala Phe Tyr Asp Val Leu Gly Thr Leu Ile Lys Pro Ser Thr
    130                 135                 140 ctg gtg cca cgc aac act cag cgc gtc caa gag gtg cct ttc tac ttc     480
Leu Val Pro Arg Asn Thr Gln Arg Val Gln Glu Val Pro Phe Tyr Phe
145                 150                 155                 160 acg ctc acg ccg cag cag gcc acc gag att gcc tcc aat cgc gac att     528
Thr Leu Thr Pro Gln Gln Ala Thr Glu Ile Ala Ser Asn Arg Asp Ile
                165                 170                 175
```

| | | |
|---|---|---|
| cgc aac agc tcc aag gtg gag cac gcc att cag gtt caa ctg cgc ttt<br>Arg Asn Ser Ser Lys Val Glu His Ala Ile Gln Val Gln Leu Arg Phe<br>        180                    185                    190 | 576 |
| tgc ctg gtg gag act tcg tgc gac cag gag gac tgc ttc ccg ccg aac<br>Cys Leu Val Glu Thr Ser Cys Asp Gln Glu Asp Cys Phe Pro Pro Asn<br>        195                    200                    205 | 624 |
| gta aac gtc aaa gtg aac aac aaa ctc tgt cag ctg cct aat gtc att<br>Val Asn Val Lys Val Asn Asn Lys Leu Cys Gln Leu Pro Asn Val Ile<br>210                    215                    220 | 672 |
| cct aca aac cga cca aat gtg gag ccc aac gct ccg ccg cga ccc gtt<br>Pro Thr Asn Arg Pro Asn Val Glu Pro Asn Ala Pro Pro Arg Pro Val<br>225                    230                    235                    240 | 720 |
| aat gtc acg tcc aat gta aag ctg tcg cct acc gtc acc aac acc ata<br>Asn Val Thr Ser Asn Val Lys Leu Ser Pro Thr Val Thr Asn Thr Ile<br>                    245                    250                    255 | 768 |
| acg gtt cag tga tgt ccg gac tac act cgt agc tac tgt ctg gcc gta<br>Thr Val Gln     Cys Pro Asp Tyr Thr Arg Ser Tyr Cys Leu Ala Val<br>        260                        265                    270 | 816 |
| tac ctg gta aag aag ctc acc tca aca cag ctt ttg cag cga atg aag<br>Tyr Leu Val Lys Lys Leu Thr Ser Thr Gln Leu Leu Gln Arg Met Lys<br>        275                    280                    285 | 864 |
| acg aag ggc gta aaa cca gcg gac tac acg cga ggc tta atc aaa gag<br>Thr Lys Gly Val Lys Pro Ala Asp Tyr Thr Arg Gly Leu Ile Lys Glu<br>290                    295                    300 | 912 |
| aag ctg act gag gat gct gac tgc gaa ata gcc acc act atg ctg aag<br>Lys Leu Thr Glu Asp Ala Asp Cys Glu Ile Ala Thr Thr Met Leu Lys<br>305                    310                    315                    320 | 960 |
| gtt tcc ctt aac tgc ccg ttg ggc aag atg aaa atg ttg ctg cct tgt<br>Val Ser Leu Asn Cys Pro Leu Gly Lys Met Lys Met Leu Leu Pro Cys<br>                    325                    330                    335 | 1008 |
| cga gca tca acc tgc tcg cat ctg caa tgc ttc gat gcc agt ctc tac<br>Arg Ala Ser Thr Cys Ser His Leu Gln Cys Phe Asp Ala Ser Leu Tyr<br>        340                        345                    350 | 1056 |
| ctg caa atg aat gag cgt aag ccc acg tgg aac tgc cct gta tgc gac<br>Leu Gln Met Asn Glu Arg Lys Pro Thr Trp Asn Cys Pro Val Cys Asp<br>                    355                    360                    365 | 1104 |
| aag ccg gcc att tat gac aac ctg gtc ata gat ggc tac ttc cag gag<br>Lys Pro Ala Ile Tyr Asp Asn Leu Val Ile Asp Gly Tyr Phe Gln Glu<br>        370                        375                    380 | 1152 |
| gtg ttg ggc tcg tcg ctt cta aag agt gat gat act gag att caa ctt<br>Val Leu Gly Ser Ser Leu Leu Lys Ser Asp Asp Thr Glu Ile Gln Leu<br>385                    390                    395                    400 | 1200 |
| cat cag gat gga tct tgg agc aca cca gga tta cgg agc gag acg cag<br>His Gln Asp Gly Ser Trp Ser Thr Pro Gly Leu Arg Ser Glu Thr Gln<br>                    405                    410                    415 | 1248 |
| atc ctt gat acg cct tca aag ccc gcc caa aag gtt gag gtt ata tcg<br>Ile Leu Asp Thr Pro Ser Lys Pro Ala Gln Lys Val Glu Val Ile Ser<br>        420                        425                    430 | 1296 |
| gat gac ata gaa ctt atc tcg gat gac gcc aag cca gta aag agg gat<br>Asp Asp Ile Glu Leu Ile Ser Asp Asp Ala Lys Pro Val Lys Arg Asp<br>435                    440                    445 | 1344 |
| ttg tcc cca gca cag gac gaa cag ccc aca tca acg tca aac agt gaa<br>Leu Ser Pro Ala Gln Asp Glu Gln Pro Thr Ser Thr Ser Asn Ser Glu<br>        450                        455                    460 | 1392 |
| act gtt gac cta acg tta agc gat tca gac gac gac atg ccg ctg gct<br>Thr Val Asp Leu Thr Leu Ser Asp Ser Asp Asp Asp Met Pro Leu Ala<br>465                    470                    475                    480 | 1440 |
| aag cgt tgt ccg ccc gcc aag caa gcc gtc gcc agt tcc acg tcg aac<br>Lys Arg Cys Pro Pro Ala Lys Gln Ala Val Ala Ser Ser Thr Ser Asn<br>                    485                    490                    495 | 1488 |

```
ggc agc ggt ggc ggc caa cgt gcc tat acc ccg gca cag cag ccc cag    1536
Gly Ser Gly Gly Gly Gln Arg Ala Tyr Thr Pro Ala Gln Gln Pro Gln
        500                 505                 510 caa tcc gag gat aat gac gaa aac tgt acg gct aag gcc aaa gag gat    1584
Gln Ser Glu Asp Asn Asp Glu Asn Cys Thr Ala Lys Ala Lys Glu Asp
                515                 520                 525 tcc gta att gat ttt cta gat tcg cca                                1611
Ser Val Ile Asp Phe Leu Asp Ser Pro
        530                 535

<210> SEQ ID NO 4
<211> LENGTH: 259
<212> TYPE: PRT
<213> ORGANISM: Drosophila melanogaster

<400> SEQUENCE: 4
```

Met Val Gln Met Leu Arg Val Val Glu Leu Gln Lys Ile Leu Ser Phe
 1               5                  10                  15

Leu Asn Ile Ser Phe Ala Gly Arg Lys Thr Asp Leu Gln Ser Arg Ile
            20                  25                  30

Leu Ser Phe Leu Arg Thr Asn Leu Glu Leu Leu Ala Pro Lys Val Gln
        35                  40                  45

Glu Val Tyr Ala Gln Ser Val Gln Glu Gln Asn Ala Thr Leu Gln Tyr
 50                  55                  60

Ile Asp Pro Thr Arg Met Tyr Ser His Ile Gln Leu Pro Pro Thr Val
 65                  70                  75                  80

Gln Pro Asn Pro Val Gly Leu Val Gly Ser Gly Gln Gly Val Gln Val
                85                  90                  95

Pro Gly Gly Gln Met Asn Val Val Gly Gly Ala Pro Phe Leu His Thr
            100                 105                 110

His Ser Ile Asn Ser Gln Leu Pro Ile His Pro Asp Val Arg Leu Lys
        115                 120                 125

Lys Leu Ala Phe Tyr Asp Val Leu Gly Thr Leu Ile Lys Pro Ser Thr
    130                 135                 140

Leu Val Pro Arg Asn Thr Gln Arg Val Gln Glu Val Pro Phe Tyr Phe
145                 150                 155                 160

Thr Leu Thr Pro Gln Gln Ala Thr Glu Ile Ala Ser Asn Arg Asp Ile
                165                 170                 175

Arg Asn Ser Ser Lys Val Glu His Ala Ile Gln Val Gln Leu Arg Phe
            180                 185                 190

Cys Leu Val Glu Thr Ser Cys Asp Gln Glu Asp Cys Phe Pro Pro Asn
        195                 200                 205

Val Asn Val Lys Val Asn Asn Lys Leu Cys Gln Leu Pro Asn Val Ile
    210                 215                 220

Pro Thr Asn Arg Pro Asn Val Glu Pro Asn Ala Pro Pro Arg Pro Val
225                 230                 235                 240

Asn Val Thr Ser Asn Val Lys Leu Ser Pro Thr Val Thr Asn Thr Ile
                245                 250                 255

Thr Val Gln

```
<210> SEQ ID NO 5
<211> LENGTH: 277
<212> TYPE: PRT
<213> ORGANISM: Drosophila melanogaster
```

```
<400> SEQUENCE: 5

Cys Pro Asp Tyr Thr Arg Ser Tyr Cys Leu Ala Val Tyr Leu Val Lys
  1               5                  10                  15

Lys Leu Thr Ser Thr Gln Leu Leu Gln Arg Met Lys Thr Lys Gly Val
             20                  25                  30

Lys Pro Ala Asp Tyr Thr Arg Gly Leu Ile Lys Glu Lys Leu Thr Glu
             35                  40                  45

Asp Ala Asp Cys Glu Ile Ala Thr Thr Met Leu Lys Val Ser Leu Asn
             50                  55                  60

Cys Pro Leu Gly Lys Met Lys Met Leu Leu Pro Cys Arg Ala Ser Thr
 65                  70                  75                  80

Cys Ser His Leu Gln Cys Phe Asp Ala Ser Leu Tyr Leu Gln Met Asn
                 85                  90                  95

Glu Arg Lys Pro Thr Trp Asn Cys Pro Val Cys Asp Lys Pro Ala Ile
                100                 105                 110

Tyr Asp Asn Leu Val Ile Asp Gly Tyr Phe Gln Glu Val Leu Gly Ser
                115                 120                 125

Ser Leu Leu Lys Ser Asp Asp Thr Glu Ile Gln Leu His Gln Asp Gly
    130                 135                 140

Ser Trp Ser Thr Pro Gly Leu Arg Ser Glu Thr Gln Ile Leu Asp Thr
145                 150                 155                 160

Pro Ser Lys Pro Ala Gln Lys Val Glu Val Ile Ser Asp Asp Ile Glu
                165                 170                 175

Leu Ile Ser Asp Asp Ala Lys Pro Val Lys Arg Asp Leu Ser Pro Ala
                180                 185                 190

Gln Asp Glu Gln Pro Thr Ser Thr Ser Asn Ser Glu Thr Val Asp Leu
                195                 200                 205

Thr Leu Ser Asp Ser Asp Asp Met Pro Leu Ala Lys Arg Cys Pro
    210                 215                 220

Pro Ala Lys Gln Ala Val Ala Ser Ser Thr Ser Asn Gly Ser Gly Gly
225                 230                 235                 240

Gly Gln Arg Ala Tyr Thr Pro Ala Gln Gln Pro Gln Gln Ser Glu Asp
                245                 250                 255

Asn Asp Glu Asn Cys Thr Ala Lys Ala Lys Glu Asp Ser Val Ile Asp
                260                 265                 270

Phe Leu Asp Ser Pro
                275
```